United States Patent [19]

Waltuck et al.

[11] Patent Number: 5,121,981
[45] Date of Patent: Jun. 16, 1992

[54] VISUAL ACUITY TESTER

[75] Inventors: Morey H. Waltuck, Sharon; Robert McKnight, Andover, both of Mass.

[73] Assignee: Mentor O & O, Inc., Norwell, Mass.

[21] Appl. No.: 116,709

[22] Filed: Nov. 3, 1987

[51] Int. Cl.$^5$ .................................. A61B 3/02
[52] U.S. Cl. ................................. 351/243; 351/246
[58] Field of Search ............... 351/239, 243, 222, 246, 351/237

[56] References Cited

U.S. PATENT DOCUMENTS

| Re. 28,921 | 8/1976 | Haines et al. |
|---|---|---|
| 3,517,988 | 6/1970 | Schwind |
| 3,639,042 | 2/1972 | Grolman |
| 3,684,355 | 8/1972 | Molmer |
| 3,705,003 | 12/1972 | Lynn et al. |
| 3,737,217 | 6/1973 | Haines et al. |
| 3,883,235 | 5/1975 | Lynn et al. |
| 3,905,688 | 9/1975 | Decker et al. |
| 3,969,020 | 7/1976 | Lynn et al. |
| 4,239,351 | 12/1980 | Williams et al. |
| 4,365,873 | 12/1982 | Ginsburg |
| 4,536,065 | 8/1985 | Sheingord ................. 351/239 |
| 4,861,156 | 8/1989 | Terry ...................... 351/243 |

Primary Examiner—Rodney B. Bovernick
Attorney, Agent, or Firm—Herbert F. Schwartz; Richard A. Inz; Gerard A. deBlasi

[57] ABSTRACT

An improved visual acuity tester is disclosed that is adapted both to measure the visual acuity of a patient and to function as an integral optical prescription calculator. The visual acuity tester essentially includes a display monitor for displaying visual acuity targets, electronic means for generating a plurality of visual acuity targets to be displayed on the monitor, and a hand-held remote control unit provided with a display unit and a keyboard coupled to the electronic means for controlling the display on the monitor and for performing prescription calculations. The visual acuity targets are created by toggling on/off the electronic means when horizontally scanning the lead lines of screen memories of the targets. Preferably, the electronic means includes a dynamic memory having two screens of memory: an active screen and an inactive screen. The active screen is displayed on the monitor and the inactive screen is being erased, both being constantly accessed at short intervals for memory refresh and erasure. Preferably, the visual acuity tester is provided with a contrast control for low contrast testing. The visual acuity tester is adjustable for straight refractory distances from about ten to about twenty feet in length. With a mirror, it also can be fitted to a shorter refractory lane.

32 Claims, 29 Drawing Sheets

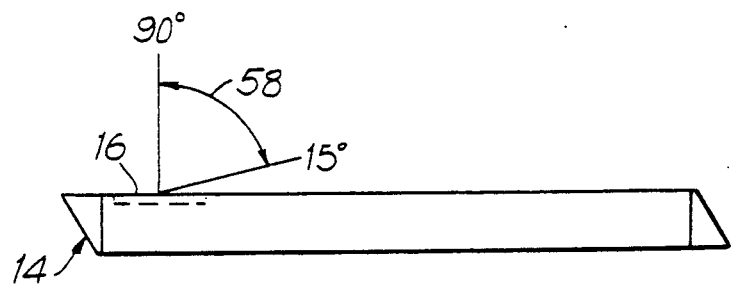
FIG. 6
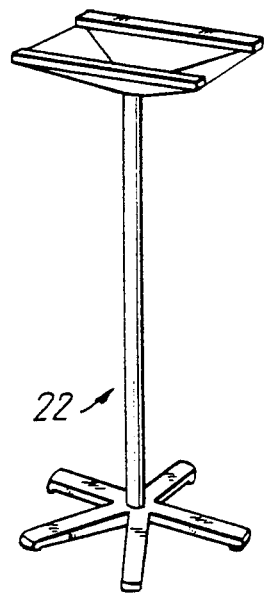
FIG. 7
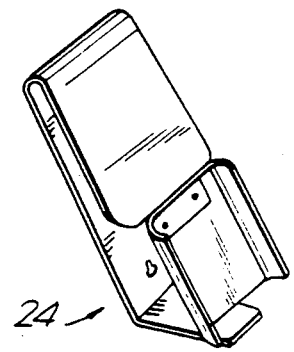
FIG. 8
FIG. 10
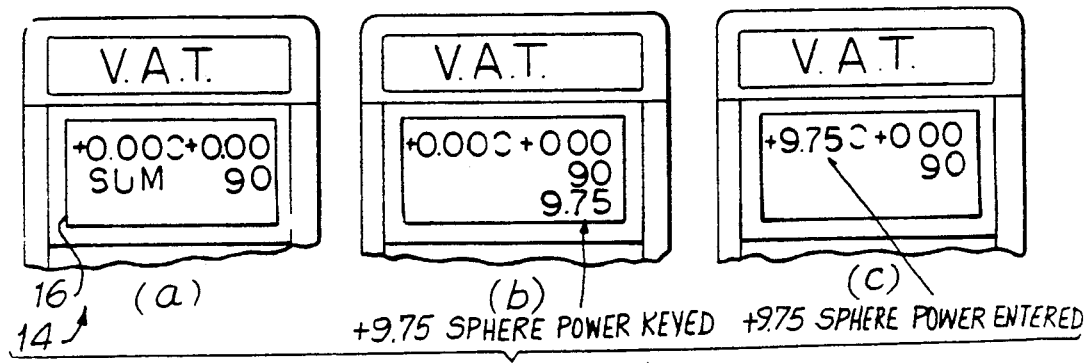

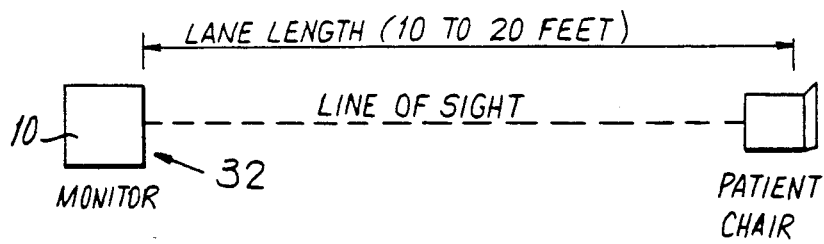
FIG. 11
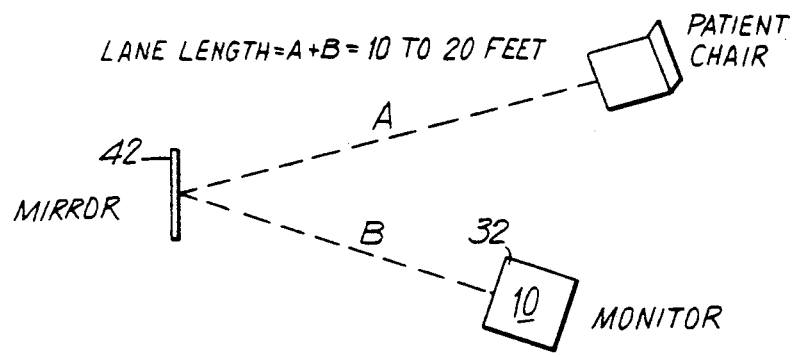
FIG. 12
FIG. 13a
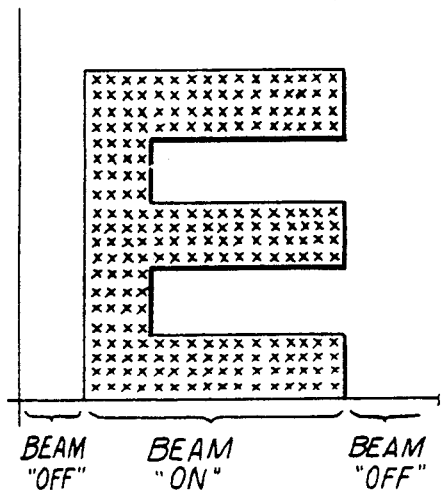
FIG. 13b
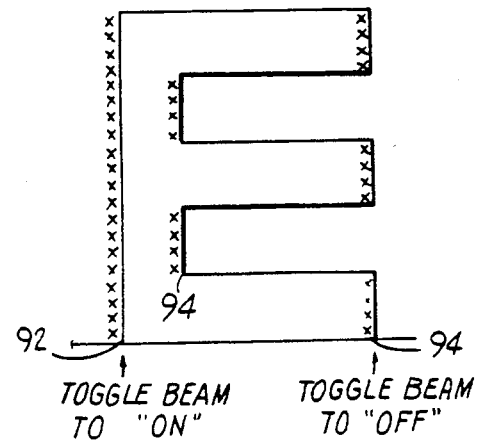

FIG. 19
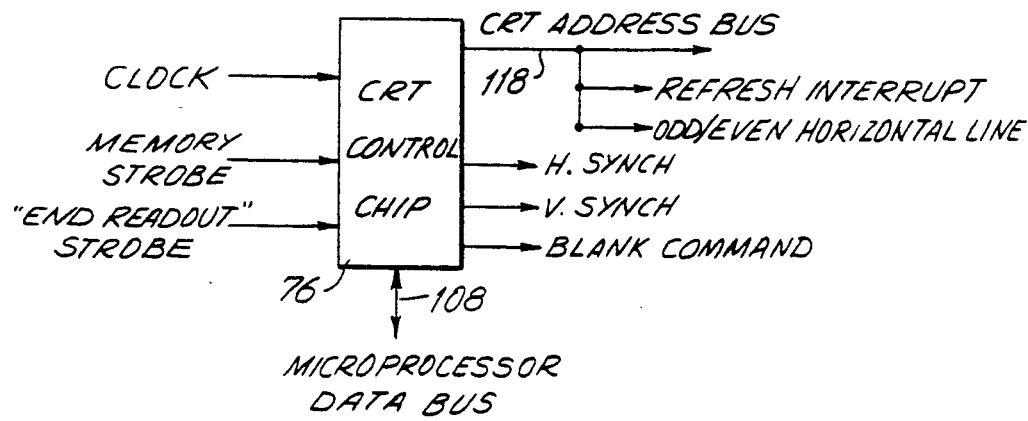
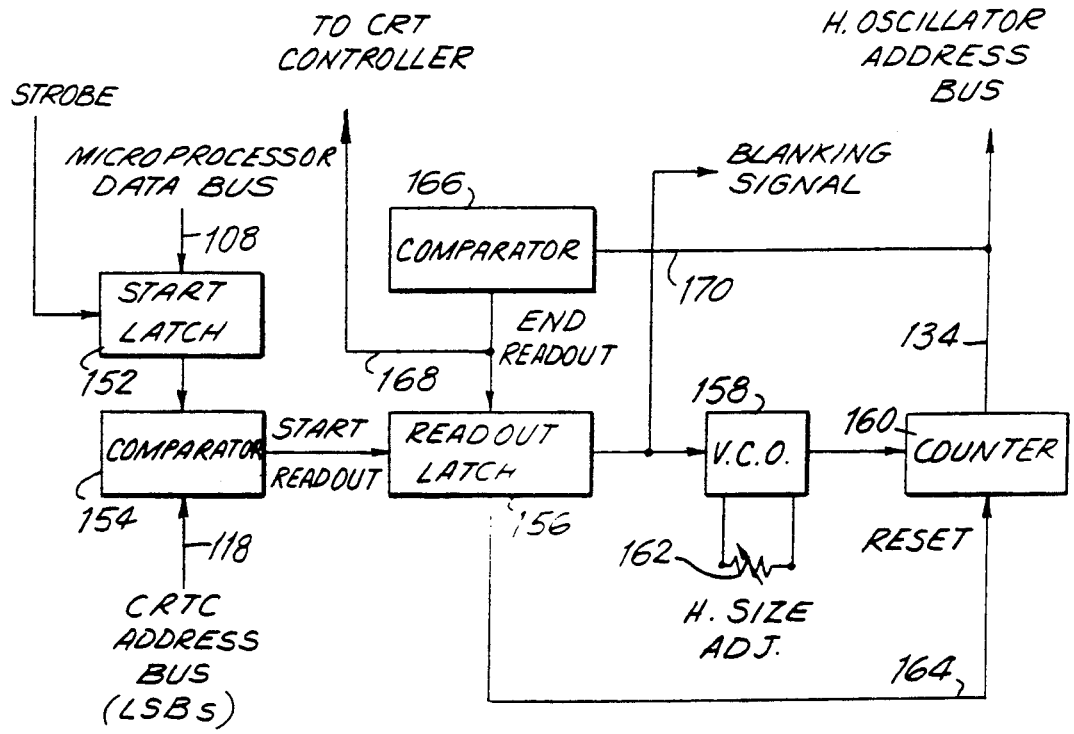
FIG. 20

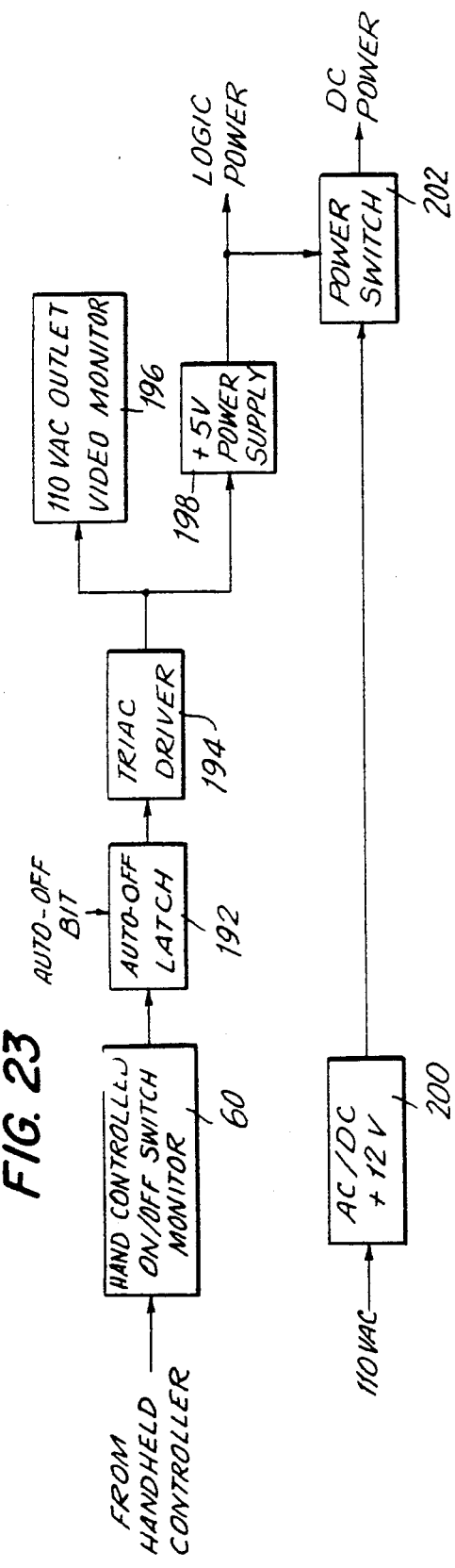
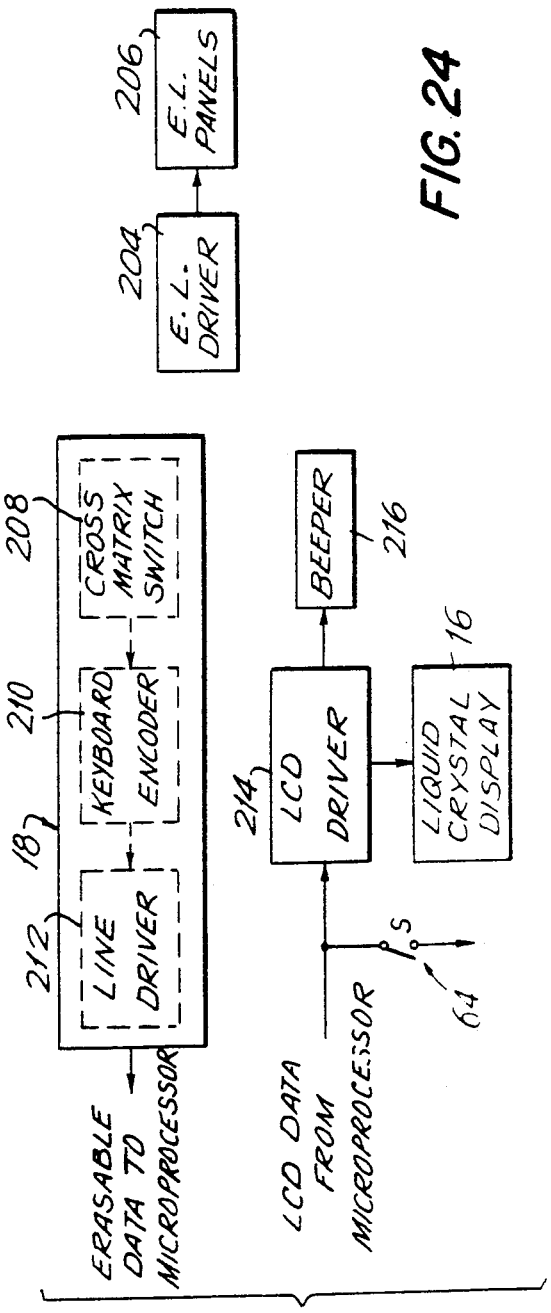
FIG. 23
FIG. 24

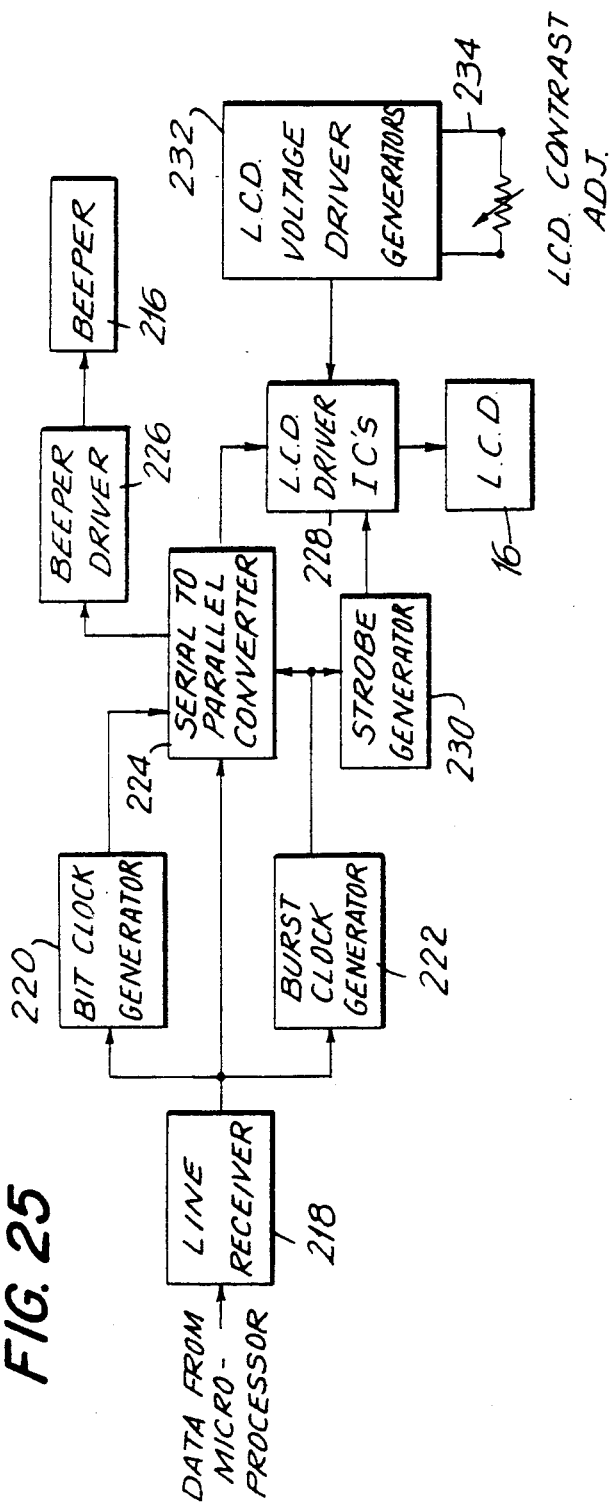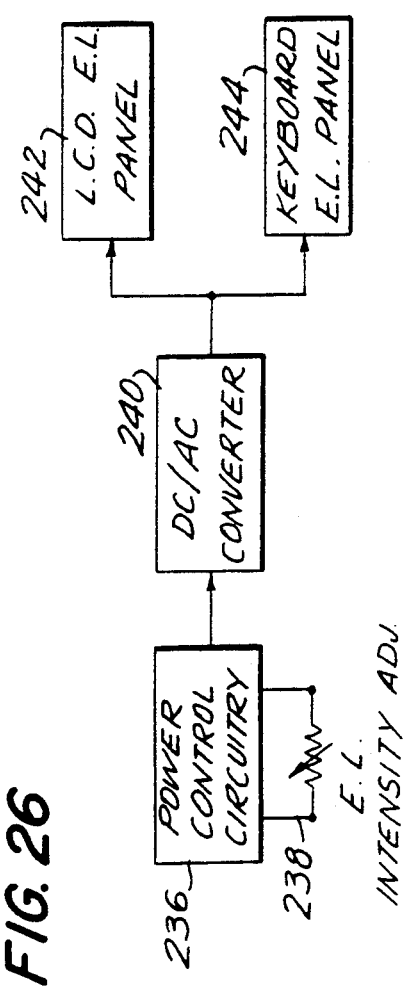
*FIG. 25*
*FIG. 26*

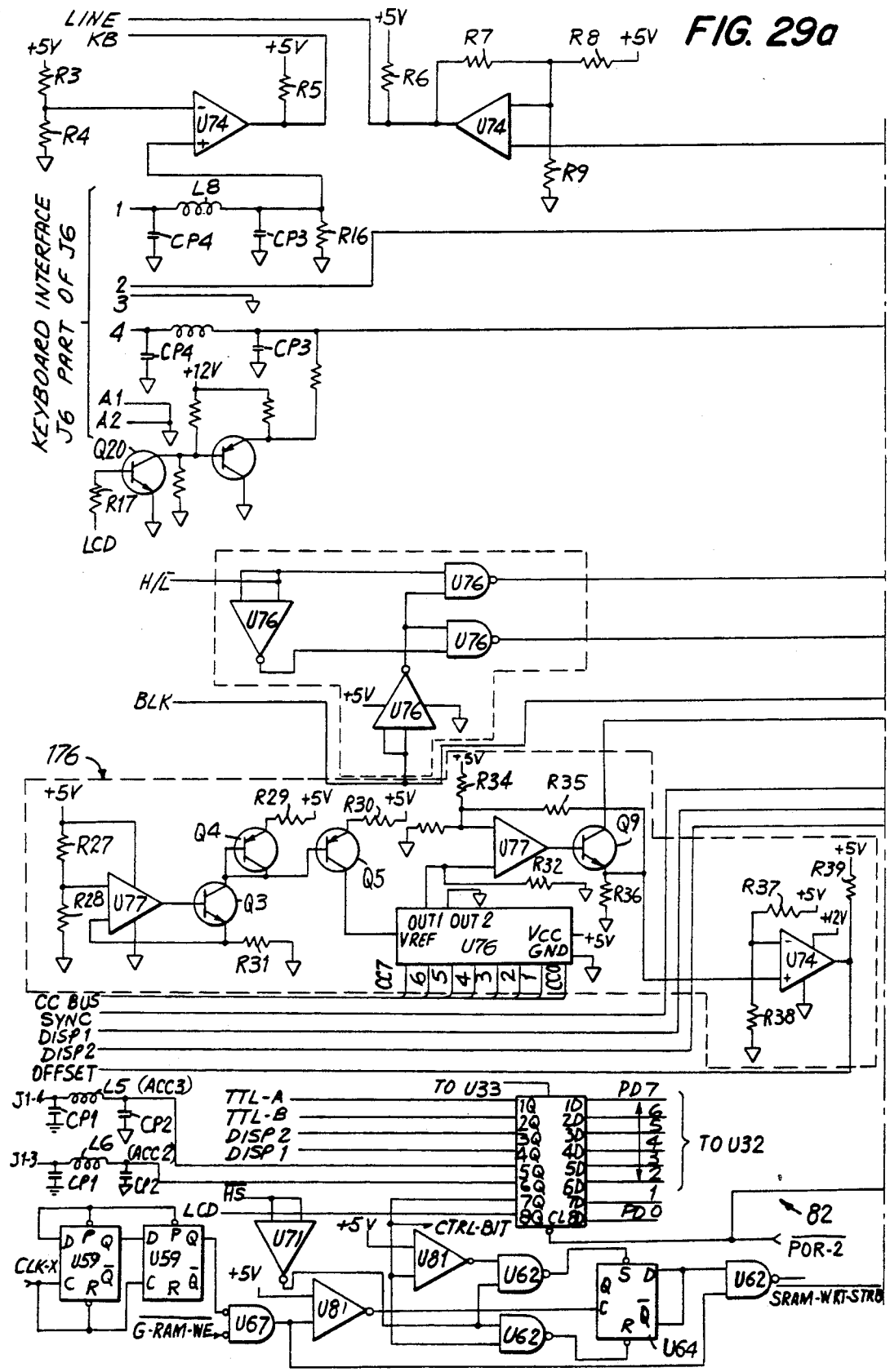

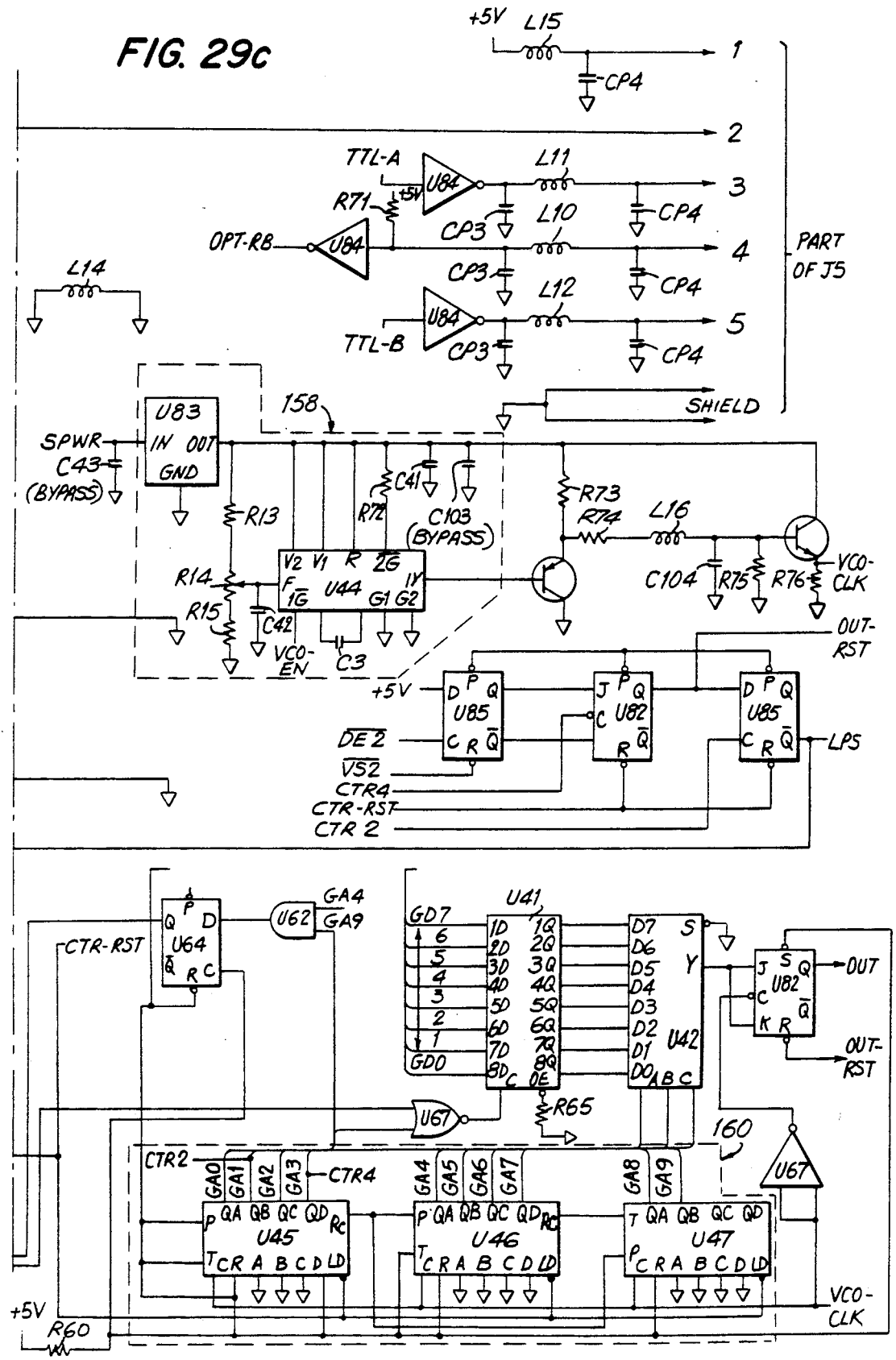

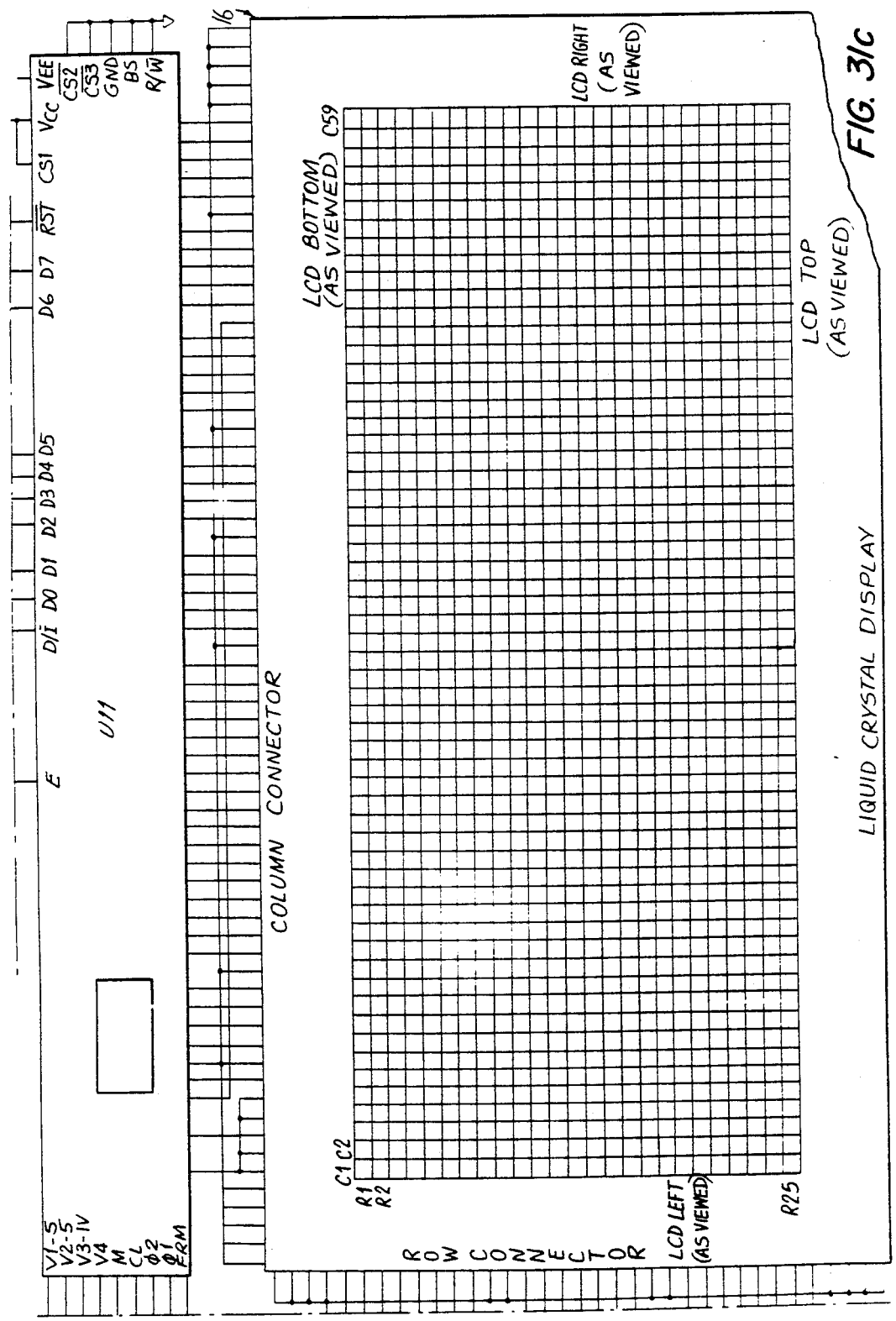
FIG. 3/c

VISUAL ACUITY TESTER

BACKGROUND OF THE INVENTION

1. Field of the Invention

The present invention relates generally to ophthalmic testing instruments and, more particularly, to an improved device adapted both to measure the visual acuity of a patient and to function as an optical prescription calculator.

2. The Prior Art

The determination of visual acuity is an essential part of every eye examination. During the course of such an examination, acuity may be measured repeatedly to ascertain the resolution of each eye independently and both eyes together. The examination may also consist of independent and combined testing of the eyes with the aid of corrective lenses. In fact, the repeated determination of acuity forms an essential part of the process of refracting or determining the optimal corrective lenses to alleviate the effects of ametropia as well as a means for assessing the progress of ocular pathology.

Originally, clinical methods for measuring visual acuity involved the use of wall charts containing a fixed array of Snellen letters, Tumbling E targets or other accepted acuity targets. The patient ordinarily viewed the charts from a fixed distance (usually 20 feet). With the advent of ophthalmic devices, clinical testing methods have become more sophisticated. One device involves the projection of targets onto screens placed at a fixed distance by means of an optical system. See U.S. Pat. No. 3,517,988. Another device employs an optical system for measuring the acuity of a low-vision patient. See U.S. Pat. No. 3,639,042. Another discloses a method for testing the glare susceptibility of a patient. See U.S. Pat. No. 3,684,355. A more sophisticated device teaches the use of a computer controlled method for the automatic visual acuity determination of a patient. See U.S. Pat. No. 3,705,003. Another automated visual examination device, one that includes a feature of mapping blind spot locations, is shown and described in U.S. Pat. No. 3,737,217. A further automated visual examination device, including fixation monitoring compensation, is described in U.S. Pat. No. 3,883,235. Another device for determining visual acuity that presents a plurality of targets seriatim is disclosed in U.S. Pat. No. 3,905,688. An automated refraction apparatus and method are disclosed in U.S. Pat. No. 3,969,020. A further automated visual examination apparatus, including mapping blind spot locations, is taught in Reissue U.S. Pat. No. Re 28,921. A device for generating and displaying visual acuity targets in a clinical setting is shown and described in U.S. Pat. No. 4,239,351. The patent discloses first and second electro-optical display devices for displaying visual acuity targets, one to be viewed by a patient and the other by an examiner. The inventions disclosed and claimed herein are improvements to U.S. Pat. No. 4,239,351.

As regards the productivity of the eye examiner, the time required to instruct the patient regarding the target he is to view, or the time the clinician requires to find, adjust and align the required target in the case of projection devices becomes increasingly important, especially with heavy patient loads. Consequently, examination time has become a critical and sparse resource for most eye examiners, one that must be husbanded carefully. There is thus room left for improvements.

SUMMARY OF THE INVENTION

It is a principal object of the present invention to provide an improved visual acuity tester adapted both to measure the visual acuity of a patient and to function as an integral optical prescription calculator.

More specifically, it is an object of the present invention to provide an improved visual acuity tester and screening device which is computer-controlled and features a high-contrast video monitor and a hand-held remote controller provided with its own built-in display unit for viewing by an eye examiner and a keyboard to operate the visual acuity tester with ease and versatility, and which enables the examiner to minimize the examination time per patient, without in any way compromising the accuracy of the examination data obtained. The improved visual acuity tester essentially comprises a display monitor for displaying visual acuity targets to be viewed by a patient, computer-controlled means for generating a plurality of visual acuity targets to be displayed on the monitor, and a hand-held remote control unit, preferably connected via a flexible cable to the computer-controlled means. The remote control unit features a display unit, which indicates to the examiner the targets that are viewed by the patient, and a lighted keyboard for controlling the selection and display of the visual acuity targets for both the patient monitor and the examiner's hand-held display unit, as well as for performing optical prescription calculations and for displaying such calculations on the hand-held display unit only for the use of the examining optician. Unlike conventional bit-mapped systems, the computer-controlled means includes a bit-mapped graphics memory that sets a bit therein to toggle its on/off state, increasing thereby the operational efficiency of the visual acuity tester. The computer-controlled means also includes a dynamic memory having two complete screens of memory of visual acuity targets either of which can be displayed on the monitor. Following the creation and display of one screen's visual acuity targets, the second screen of visual acuity targets is erased in preparation for the creation of the next screen of visual acuity targets. This erasure in advance of the display of the second of the two complete screens further increases the operational efficiency of the visual acuity tester by minimizing response delays therein. Both screens of memory are being constantly accessed at short intervals for memory refresh. Preferably, the visual acuity tester is provided with contrast control for low contrast testing. Preferably, the visual acuity tester is adjustable for straight refractory distances between about ten to about twenty feet in length and, with the aid of a mirror, it also can be fitted to shorter refractory lanes.

Other objects of the present invention will in part be obvious and will in part appear hereinafter.

The invention accordingly comprises the visual acuity tester of the present disclosure, its components, parts and their interrelationships, the scope of which will be indicated in the appended claims.

BRIEF DESCRIPTION OF THE DRAWINGS

For a fuller understanding of the nature and objects of the present invention, reference is to be made to the following detailed description, which is to be taken in connection with the accompanying drawings, wherein:

FIG. 6 is a side elevation of the third operative part shown in FIG. 3 and illustrates the viewing angle range of its display;

FIG. 7 illustrates, in perspective, an optional accessory for the two operative parts illustrated in FIG. 1;

FIG. 8 illustrates, in perspective, am optional accessory for the third operative part illustrated in FIG. 3;

FIG. 10 illustrates the alternate utilization of the visual acuity tester as a device for performing optic-specific calculations;

FIG. 11 illustrates a straight refracting lane;

FIG. 12 illustrates a refracting lane with the aid of a mirror;

FIGS. 13(a) and 13(b) illustrate and contrast an operative feature of the visual acuity tester of the invention with testers of the prior art;

FIG. 19 is a block diagram of a fourth operative segment of the part illustrated in FIG. 14;

FIG. 20 is a block diagram of a fifth operative segment of the part illustrated in FIG. 14;

FIG. 23 is a block diagram of an eighth operative segment of the part illustrated in FIG. 14;

FIG. 24 is a block diagram of the third operative part illustrated in FIG. 3;

FIG. 25 is a block diagram of one operative segment of the part illustrated in FIG. 24;

FIG. 26 is a block diagram of a second operative segment of the part illustrated in FIG. 24;

FIGS. 28a-d, 29a-c, and 30a-d (hereinafter collectively referred to as FIGS. 28, 29 and 30) are schematic circuit diagrams of other operative segments of one of the two operative parts illustrated in FIG. 1; and FIGS. 31a-d (hereinafter collectively referred to as FIG. 31) are schematic circuit diagrams of the third operative part illustrated in FIG. 3.

DETAILED DESCRIPTION OF THE PREFERRED EMBODIMENT

In general, the illustrated embodiment of an improved visual acuity tester, designed both to measure the visual acuity of a patient and also to function as an integral optical prescription calculator, comprises a display monitor 10 for displaying visual acuity targets, means 12 for generating a plurality of visual acuity targets to be displayed on the monitor 10, and a hand-held remote control unit 14.

As mentioned, the determination of visual acuity is an essential part of every eye examination. During an eye examination, acuity is repeatedly measured to ascertain first the resolution of each eye independently and second, for both eyes together. The repeated determination of acuity is an essential part of the process of refracting. Following the determination of the optimal corrective lenses, if any, the examiner frequently needs to perform optic-specific calculations to enable him/her to write a prescription for the just examined patient. In order to facilitate this second necessary task, the visual acuity tester of the invention also is adapted to function as an integral optical prescription calculator, as will be more evident from below.

Figure 4:
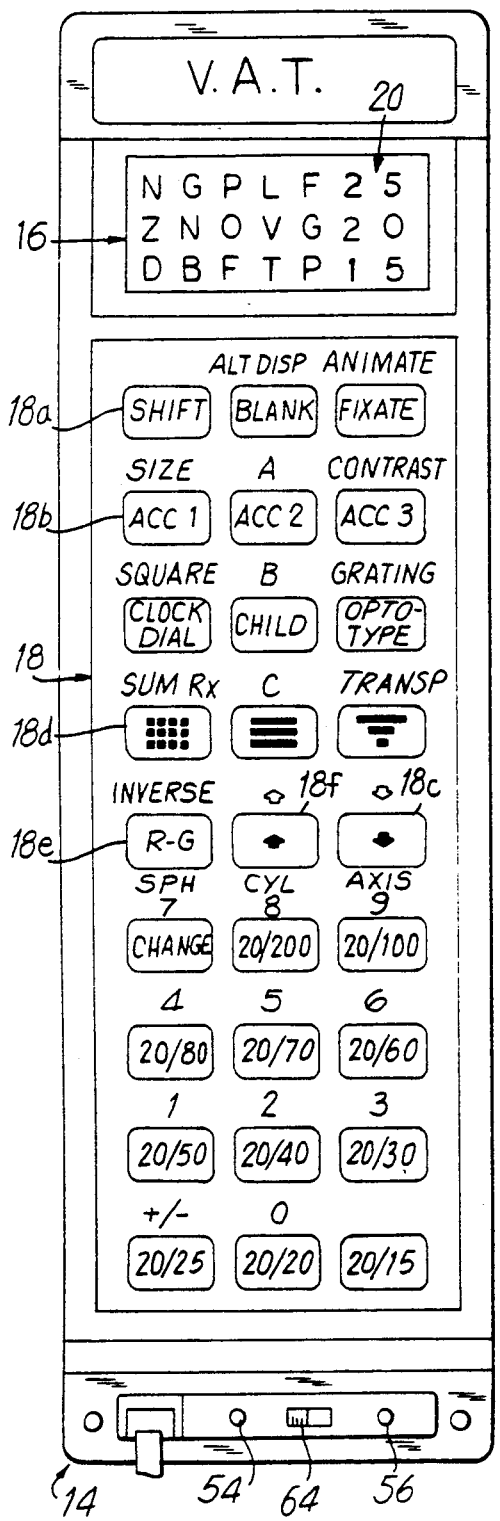
FIG. 4 is an enlarged plan view of the third operative part shown in FIG. 3.

As may be best observed in FIG. 4, the hand-held remote control unit 14 is provided with its own integral display unit 16 and a keyboard 18. The integral display unit 16 shows to the examiner precisely what is being displayed for the patient on the monitor 10. In addition, the display unit 16 also informs the examiner of the acuity of the targets being displayed, as at 20, information not shown on the patient monitor 10. While performing optical prescription calculations, data is displayed only on the display unit 16 of the hand-held remote control unit 14; the patient monitor 10 is blank.

Figure 9:
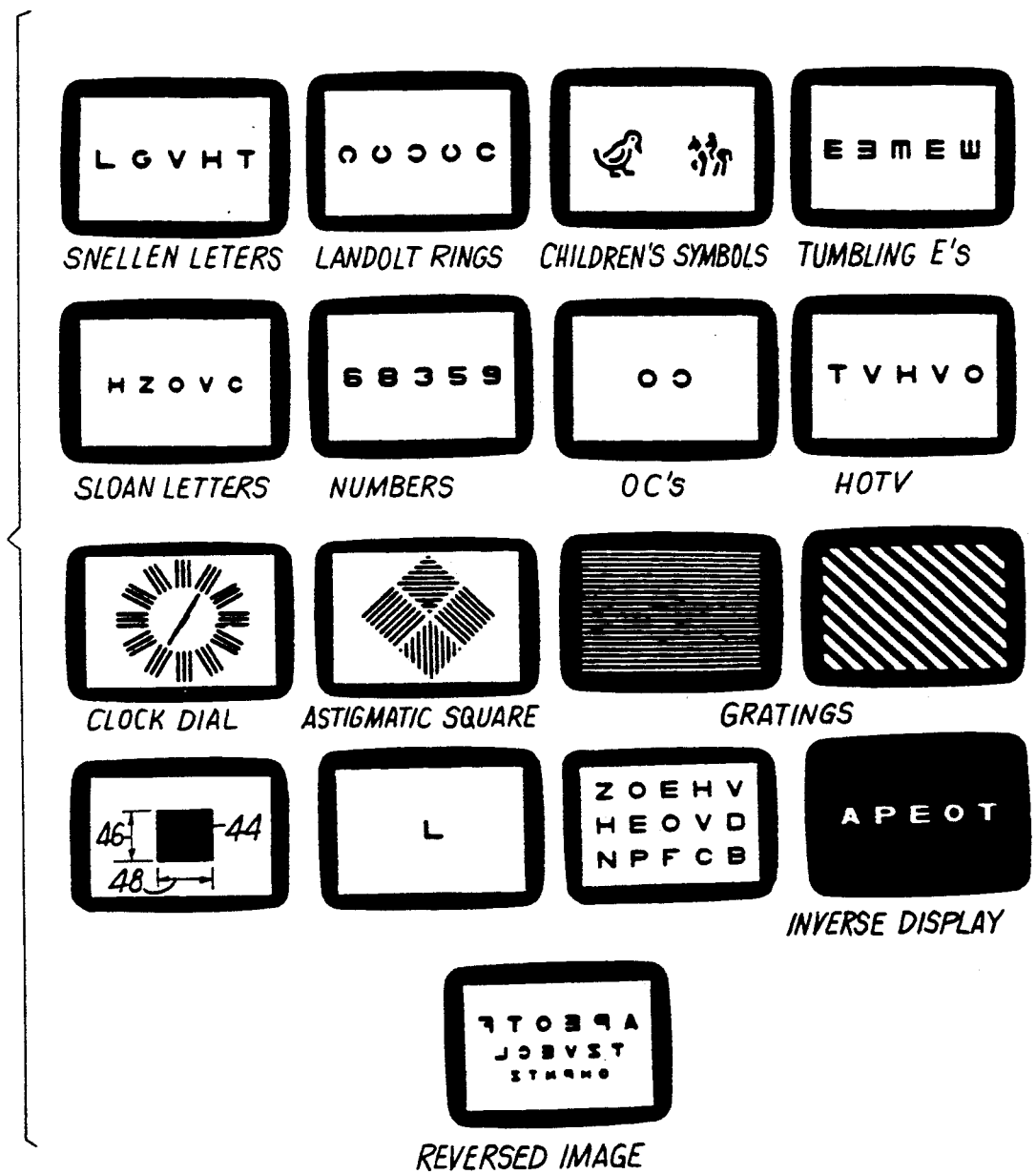
FIG. 9 illustrates a plurality of visual acuity targets which can be displayed on the patient monitor of the visual acuity tester.

The keyboard 18 of the hand-held remote control unit 14 allows the eye examiner, without moving from his (or her) examining position, to control the display of a plurality of acuity targets on the monitor 10 and also to perform the optical prescription calculations. Some of the plurality of acuity targets designed to be displayed on the patient monitor 10 are illustrated in FIG. 9, and include Snellen and Sloan letters, Landolt rings, children's symbols, tumbling E's, gratings and other phototypes for acuity testing. By pressing the keyboard 18 controls, the examiner can change acuity sizes gradually from 20/15 to 20/200 or shift directly to the acuity size of his choice.

Acuity targets or their screen configuration can be changed quickly and simply by alternatively pressing the various controls on the keyboard 18 to suit the situation and the patient. The examiner can, inter alia, display an astigmatic clock dial, with or without a movable pointer, invert the color of the display monitor 10, effect a reversed image or contrast control for performing low contrast testing. The specific visual acuity targets selected by the examiner and appearing on the display monitor 10 are reliable, clearly delineated precision character sizes.

Preferably, the display monitor 10 is built as an independent unit and designed to sit on top of the cabinet housing the means 12 for generating the plurality of visual acuity targets. Of course, if desired, the two operative parts, i.e., the display monitor 10 and the means 12, also can be constructed as one unit. The two operative parts 10 and 12 can be placed on a desk or any other support, such as a floor stand 22 illustrated in FIG. 7.

Preferably, the horizontal center of the display monitor 10 should be located at the average patient eye level. An optional stand 24 for the hand-held remote control unit 14 also is provided and is illustrated in FIG. 8. This stand 24 can accommodate the hand-held remote control unit 14 in a horizontal position as when placed on a desk-top, or it can accommodate the unit 14 in a vertical position, with the stand 24 screwed to a vertical wall. Of course, the hand-held remote control unit 14 can simply be placed by the examiner on his desk, next to his note pad and left there until needed. A power cord 26, when plugged into any three-pronged outlet, is designed to bring 110 VAC, 50/60 Hz power to the visual acuity tester. A further power cord 28 couples power from the means 12 to the monitor 10. A video cable 30, with an adapter, couples the video signals generated by the means 12 to the monitor 10 to be displayed on a screen 32 thereof. Another flexible cable 34 of sufficient length, preferably forty feet or more, is designed to be bayonet-connected, as at 36, to the bottom end of the hand-held remote control unit 14.

Figure 5:
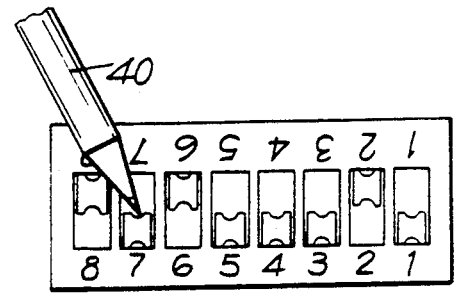
FIG. 5 is an enlarged elevation of a portion, illustrating selector switch settings, from one of the parts illustrated in FIG. 2.

The back panel of the means 12 for generating the plurality of visual acuity targets also is provided with a plurality of selector switch settings 38, illustrated on an enlarged scale in FIG. 5. For the most part, these selector switch settings 38 determine only initial values upon startup or resetting, which values can be conveniently changed at any time by pressing an appropriate control key on the keyboard 18 of the hand-held remote control unit 14.

There are eight selector switch settings 38 shown, each switch being adjustable between an up or down position. The switch settings 38 can be set with the aid of any sharp, pointed object, such as a penpoint 40. These initial selected values, depending upon the up or down positions of the respective switch settings 38 are as follows:

Switch #1, in the up position reverses the video image for use with a single mirror as illustrated in FIG. 12 and, in the down position effects normal video image for use without a mirror, as illustrated in FIG. 11, or with two mirrors. Switch #2, in the up position displays black characters on white background (normal); in the down position displays white characters on black background (inverse display). Switch #3, in the up position, video displays squared letters; in the down position, video displays Snellen/Sloan letters. Switch #4, in the up position, left- and right- facing tumbling E's, Landolt rings, gratings, and OC's on Hand Controller display are reversed to match direction patient should point when examiner faces patient; in the down position, Hand Controller display is identical to video display. Switch #5, in the up position, letter optotype is Sloan letters; in the down position, letter optotype is conventional Snellen letters. Switch #6, in the up position displays computerized prescription to the nearest one-quarter diopter; in the down position displays computerized prescription to the nearest one-eighth diopter. Switch #7, in the up position, cylinder value entered in SUM Rx mode assumed to be a "−" until the "+/−" key is pressed. In the down position, cylinder value entered in SUM Rx mode assumed to be a "+" until the "+/−" key is pressed. Switch #8, in the up position, Hand Controller emits short tone on each keystroke; in the down position, Hand Controller is silent.

During the initial setup of the visual acuity tester of the invention, the tester must first be calibrated for the patient refracting distance in the examiner's office. The visual acuity tester of the invention is provided with a full resolution image size that is variable to accommodate varying refracting distances between about ten and twenty feet, observe FIGS. 11 and 12. The patient refracting distance in a straight refracting lane, as in FIG. 11, is measured directly between the display monitor screen 32 and the patient's eyes. When a mirror 42 is used, as in FIG. 12, the patient refracting distance is the sum of the screen 32 to the mirror 42 distance and of the mirror 42 to the patient's eyes distance. In either event, when the measured refracting distance is less than twenty feet, for which distance the tester is originally calibrated, the size of the image on the screen 32 must be reduced in size, both vertically and horizontally, such that the visual acuity targets appearing thereon always subtend at a precise certain angle.

The calibration is effected as follows. With the patient refracting distance measured to the nearest one-half foot, the "Shift" control key 18a on the hand-held remote control unit 14 is depressed, followed by pressing the "Size" control key 18b. As a consequence, a calibration square 44 of 3"×3", observe FIG. 9(a), appears on the screen 32 of the display monitor 10. Simultaneously therewith, the following legend appears on the display unit 16 of the hand-held remote control unit 14: "3 IN SQ - FOR 20.0' - VIEW DIST." Then by pressing the control key 18c on the hand-held remote control unit 14, marked with a downward facing arrow, this initial viewing distance value on the display unit 16 will decrease by one-half foot each time the control key 18c is pressed and the calibration square 44, originally set at 3"×3", will increase slightly in size. Control key 18c is continuously depressed until the measured patient refracting distance appears on the display unit 16. It now becomes necessary to adjust, that is to shrink the now enlarged calibration square 44. Note arrow 46 for denoting the vertical height of the square 44 and arrow 48 for denoting the horizontal width thereof. By using a small screwdriver, a HEIGHT adjustment screw 50, located on the front control panel of the display monitor 10, is turned until the enlarged calibration square 44 is once again three inches in height. With the same screwdriver, a HORIZONTAL SIZE adjustment screw 52, located on the back panel of the means 12 for generating the plurality of visual acuity targets, is turned until the enlarged calibration square 44 is once again three inches in width. The circuitry to accomplish the above will be described below.

Next, the examiner may wish to adjust the brightness of the display unit 16 and of the keyboard 18 and, the contrast of the display unit 16 of the hand-held remote control unit 14 for his (or her) individual preference. By using the same small screwdriver, a brightness adjustment screw 54, located on the bottom panel of the control unit 14, is turned until both the display unit 16 and the keyboard 18 are illuminated at the intensity level desired. Then, with the hand-held remote control unit 14 held by the examiner in position as he (or she) would normally use it, a viewing angle adjustment screw 56, located adjacent the brightness adjustment screw 54, is turned until the display unit 16 is at its maximum contrast within a range 58 of viewing angle from about 15° to about 90°; i.e., matching the optimal contrast to the user's usual viewing angle.

Each of the three operative parts 10, 12 and 14 of the visual acuity tester is provided with its own ON/OFF power switch as follows: a display monitor switch 60, a switch 62 on the back panel for the means 12 for generating the visual acuity targets and a switch 64 for the hand-held remote control unit 14, located in between the screws 54 and 56. During normal operation, the switches 60 and 62 are to remain ON. This allows the visual acuity tester of the invention to be turned ON or OFF by manipulating the switch 64 only. At the end of the day, only switch 64 needs to be turned OFF.

The front panel of the means 12 for generating the plurality of visual acuity targets is provided with a fixation light 66 and a red-green display 68 to administer the well-known red-green test. If the visual acuity tester of the invention remains unused for a predetermined time, say about ten minutes or so, the display monitor 10 will automatically change to and display a blank screen from whatever image it may have displayed before. Simultaneously, the fixation light 66 will light. Visual acuity targets can thereafter be once again displayed on the display monitor screen 32 by pressing any of the control keys on the hand-held remote control unit 14. The visual acuity tester of the invention, furthermore, is provided with an automatic shut-off, which is actuated any time the tester remains unused for an extended period of predetermined time, usually about four hours. Once the visual acuity tester is turned off in this manner, it is reactivated by turning the switch 64 on the hand-held remote control unit 14 first to OFF and then back to ON.

Preferably, the display monitor 10 includes a black and white raster scanned cathode ray tube (CRT). If desired, a long persistence phosphor tube also can be employed to reduce any perceptible flicker on the screen 32 due to the 30 Hz interlaced memory refresh scheme, adverted to below. Preferably, the display unit 16 on the hand-held remote control unit 14 is a backlighted liquid crystal display unit, with the keyboard 18 also being backlighted.

Most of the operational electronics of the visual acuity tester of the invention are contained within the means 12 for generating the plurality of visual acuity targets. Some electronics also are contained within the hand-held remote control unit 14, both as more fully described below. While both the display monitor 10 and the means 12 for generating the plurality of visual acuity targets operate with high internal voltages, the hand-held remote control unit 14 is designed to operate on low voltage for additional operator safety.

Figure 14:
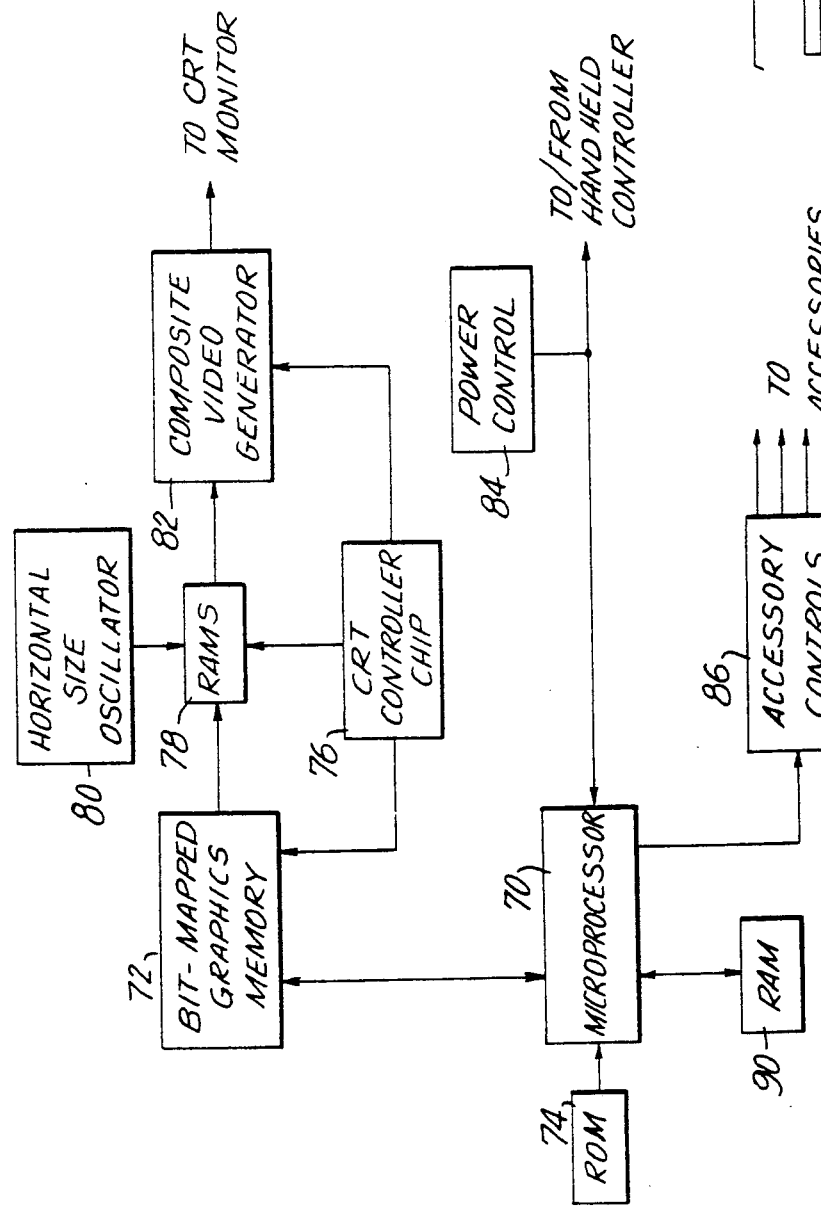
FIG. 14 is a block diagram of the means for generating a plurality of visual acuity targets to be developed on the patient monitor.

A block diagram of the means 12 for generating the plurality of visual acuity targets is shown in FIG. 14. The means 12 for generating the plurality of visual acuity targets is a microprocessor based unit and includes a bit-mapped graphics memory 72 having two complete screens of memory, either of which can be displayed at the display monitor 10. One screen of memory contains 512×400 pixels' worth of CRT image data, i.e., 512 pixels for each of the 400 horizontal lines. Following the generation and display of one screen's visual acuity targets, the second screen is erased in the memory 72. By thus in effect erasing in advance, the visual acuity tester of the invention saves time, decreasing thereby any potential response delays of the tester. The microprocessor 70 runs a program stored in a program memory, which is a ROM 74. The microprocessor 70 reads from and writes to the bit-mapped graphics memory 72. A CRT controller chip 76 is used to control the readout from the bit-mapped graphics memory 72. The CRT controller chip 76 is designed to create all addressing, synchronization and blanking signals required to generate a full resolution screen size CRT image on the screen 32 of the display monitor 10. As mentioned, this full resolution CRT image size is variable to accommodate patient refracting distances between about ten and twenty feet, note FIGS. 11 and 12.

Electronically, the image size shrinking of the calibration square 44, FIG. 9(a), is effected as follows. The vertical shrinking of the calibration square 44, along the arrow 46, is accomplished by utilizing the built-in vertical size adjustment of the CRT display monitor 10 itself. CRT monitors, as a rule, have a very limited range of adjustment of the horizontal size, however. This shortcoming of the CRT monitors necessitates the use of a pair of buffer RAMS 78, operated in conjunction with a horizontal size oscillator 80 and a composite video generator 82, in such a manner that read out to the CRT display monitor 10 occurs at a variable rate of speed, producing thereby a variable sized image of the calibration square 44 along the horizontal arrow 48.

During any given horizontal line time, as timed by the CRTC chip 76, one buffer RAM of the pair of buffer RAMS 78 is being written into by the CRT controller chip 76 while, at the same time, the other buffer RAM of the pair of buffer RAMS 78 is being read out, via the horizontal oscillator 80 and counter 160, to the CRT display monitor 10 via the composite video generator 82. During the next succeeding horizontal line time, the respective roles of the pair of buffer RAMS 78, as above described, are reversed. Once the horizontal size shrinking of the calibration square 44 is completed, the rate of speed of the readout of the pair of buffer RAMS 78 to the CRT display monitor 10, via the composite video generator 82, is stabilized and remains the same thereafter. A power control 84 establishes communication from the hand-held remote control unit 14, permitting all power to the means 12 for generating the visual acuity targets, save power to a switch monitoring circuitry 60, to be controlled from the control unit 14.

Figure 1:
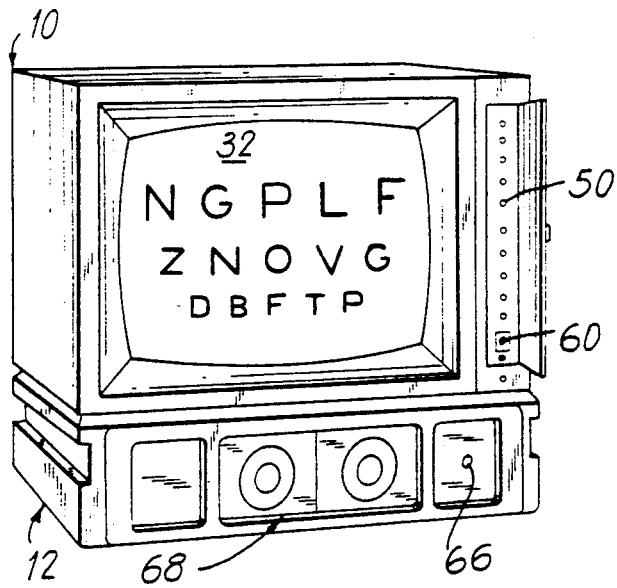
FIG. 1 is a perspective view of two operative parts of the three-part visual acuity tester embodying the present invention.
Figure 2:
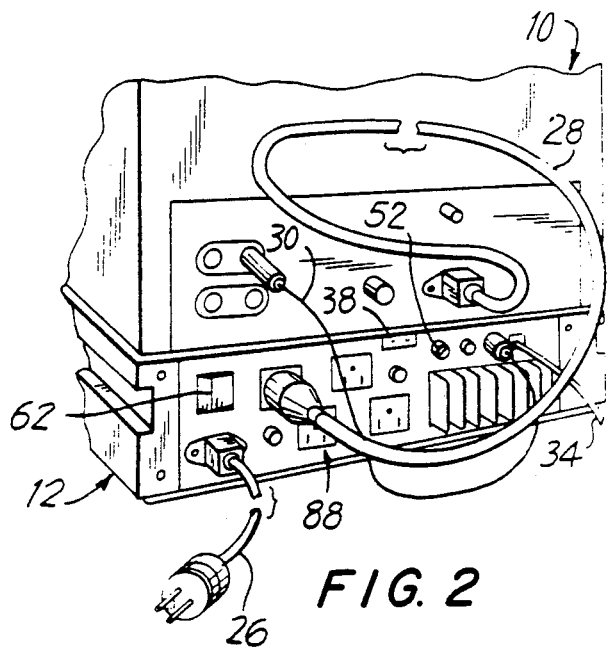
FIG. 2 is a rear partial perspective view of the parts shown in FIG. 1.
Figure 3:
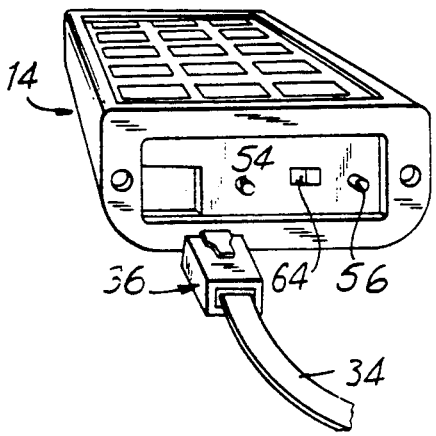
FIG. 3 is a perspective view of a third operative part of the three-part visual acuity tester.

The microprocessor 70 also monitors all command signals generated by manipulating the keyboard 18 controls and arriving from the hand-held remote control unit 14 via the forty-foot flexible cable 34. Further, the microprocessor 70 takes appropriate action, upon receipt of command signals, by writing instructions to the bit-mapped graphics memory 72 and to the liquid crystal display unit 16 of the hand-held remote control unit 14. In addition, the microprocessor 70 also controls all connected accessories via an accessory control 86. Accessories include the fixation light 66, the red-green display 68, and three additional items, any one of which can be plugged into one of the three line voltage outlets 88 located on the back panel of the means 12 for generating the plurality of visual acuity targets, observe FIG. 2. Such additional items can include a second display monitor, not shown, which can be used for near-vision or low-vision testing, room lighting, and other like instruments. Finally, a scratch-pad RAM 90 also is connected in two-way communication to the microprocessor 70. The function of the scratch-pad RAM 90 is to store temporarily data required for program execution.

As mentioned, the operation of the bit-mapped graphics memory 72 of the means 12 for generating the plurality of visual acuity targets entails a unique feature. This unique feature will be described with reference to FIG. 13 where the generation of one visual acuity target, herein the letter "E" at 20/20 acuity size, is illustrated. In conventional prior art bit-mapped systems, as illustrated in FIG. 13(a), a bit is set in the bit-mapped memory for each pixel of the image which is to be generated, i.e., displayed on the screen of a display monitor. An "x" in FIG. 13(a) and in FIG. 13(b) indicates that a bit is so set. Consequently, in such prior art systems, 153 bits must be set by the processor in the bit-mapped memory in order to generate the illustrated letter "E" at the 20/20 acuity size. In contrast and as illustrated in FIG. 13(b), the visual acuity tester of the invention has its microprocessor 70 work at a greatly improved efficiency. In the visual acuity tester of the invention, the microprocessor 70 sets a bit in the bit-mapped graphics memory 72, not when the horizontally scanning beam is "on", as in the prior art system of FIG. 13(a), but rather to toggle the "On/Off" state of the horizontally scanning beam when scanning the leading edges of the target, as at 92 and 94, to create a memory pattern illustrated in FIG. 13(b). Thus, for the identical letter "E" at the 20/20 acuity size, now only thirty bits need be written by the microprocessor 70 to be set in the bit-mapped graphics memory 72. The resultant improvement in operational efficiency translates into a much faster visual acuity target generation, making real-time generation of targets possible with relatively slow and less powerful, and thus less expensive, hardware. As is evident, the larger the visual acuity target to be created, the greater is the increase in efficiency. With a letter "E" at the illustrated acuity size of 20/20, a five-fold increase in efficiency is achieved. At an acuity size of 20/200, a 102-fold efficiency improvement is effected.

Figure 15:
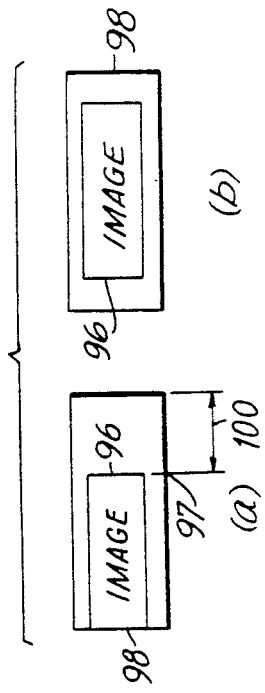
FIG. 15 is a diagram illustrating another operative feature of the invention.

After the visual acuity tester of the invention has been properly calibrated for the exact patient refracting distance between about ten to about twenty feet, it is preferable that the image is horizontally centered on the CRT display monitor 10. This horizontal centering of an image 96 will be described with reference to FIG. 15. In essence, horizontal centering of the image 96 is effected by delaying the readout of the pair of buffer RAMS 78 to the CRT monitor 10 until the CRT beam is in the midst of its horizontal sweep. The CRT controller chip 76 is now always loading the pair of buffer RAMS 78 at a constant rate of speed corresponding to a full screen size image. The CRT controller chip 76 addresses increment as the beam scans. The least significant bits (LSBs) of these addresses are used as an indication of horizontal beam position.

The readout of the pair of buffer RAMS 78 is started when the LSBs of the CRT controller chip 76 addresses match a value loaded into a "start register" 152 (observe FIG. 20) and continues at a rate set by the horizontal size oscillator 80 until the entire line has been read out. Then, the readout termination address is detected by the pair of buffer RAMS 78, the readout therefrom is stopped, and the beam is blanked for the remainder of the horizontal sweep. In order to determine what value is to be loaded into the "start register," the microprocessor 70 first loads a value of zero therein. This causes the pair of buffer RAMS 78 readout to start at the far left edge of the screen 98, as indicated in FIG. 15(a), with the image 96 ending at some point, as at 97, along the horizontal sweep. The detection of the readout termination address in mid-sweep at point 97 actuates a "light pen strobe" input on the CRT controller chip 76, which latches the CRT controller address at the time of its occurrence. This latched value is read by the microprocessor 70. The LSBs of this latched value indicate when horizontally across the screen 98 the beam was located when the termination address was detected. From this, the microprocessor 70 calculates the distance, indicated by an arrow 100, from the right edge of the image 96 to the right edge of the screen 98. The calculated value is now halved and loaded into the "start register 152," as a consequence, the image 96 is centered, as illustrated in FIG. 15(b).

Figure 16:
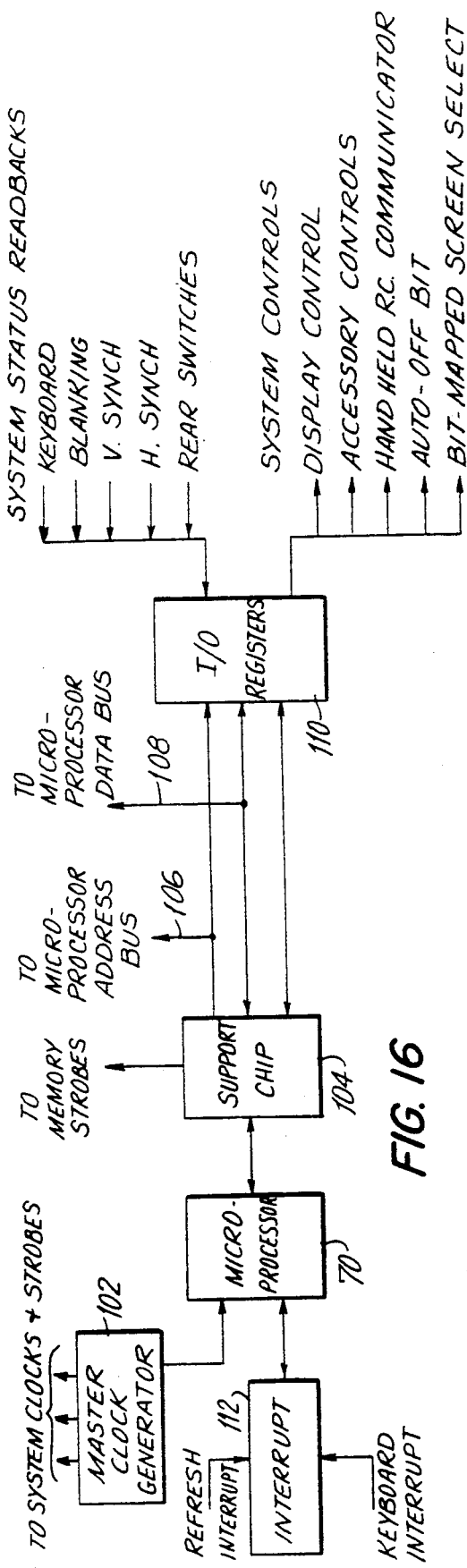
FIG. 16 is a block diagram of one operative segment of the part illustrated in FIG. 14.

In FIG. 16 is illustrated the microprocessor 70 and its immediately associated circuitry. Timing for the microprocessor 70 is provided by a master clock generator 102. Support chips (i.e., integrated circuits) 104 enhance its operation, communicating with memory strobes, a microprocessor address bus 106, a microprocessor data bus 108, a plurality of I/O registers 110, having, inter alia, system status readbacks, including keyboard, blanking, vertical synchronization, horizontal synchronization, and rear switches. The microprocessor 70 also is in two-way communication with an interrupt circuit 112, for inputting into the microprocessor 70 either "refresh interrupt" signals or "keyboard interrupt" signals.

Figure 17:
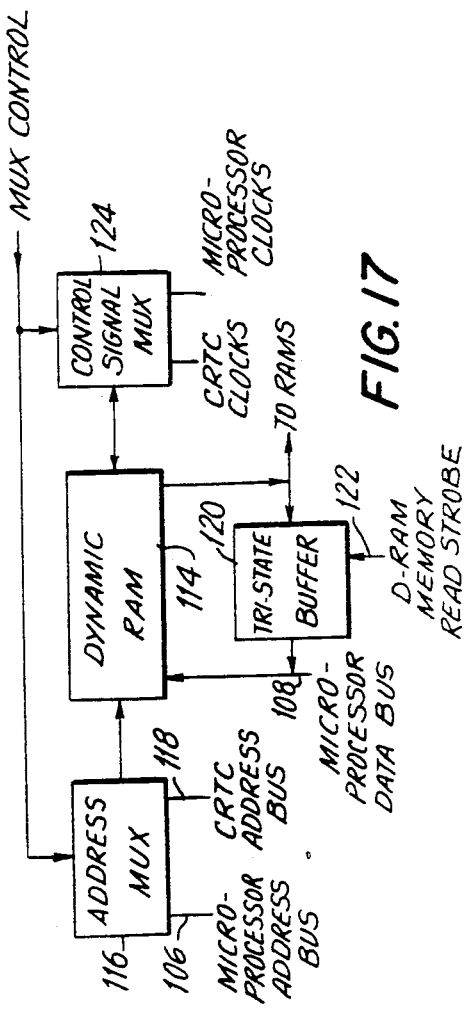
FIG. 17 is a block diagram of a second operative segment of the part illustrated in FIG. 14.

In FIG. 17 are illustrated the building blocks comprising the bit-mapped graphics memory 72, which include a dynamic RAM 114, addressed via an address multiplexer 116 from a multiplexer control. Address multiplexer 116 is connected to the microprocessor address bus 106 and a CRTC address bus 118. A tri-state buffer 120 couples the dynamic RAM 114 to the microprocessor data bus 108 and is controlled by a dynamic RAM memory read strobe 122. A control signal multiplexer circuit 124, also connected to the multiplexer control, provides control signals to the dynamic RAM 114, as provided by clocks from the CRTC clocks and the microprocessor clocks. Dynamic ram 114 also is coupled to the pair of buffer rams 78.

Thus, the bit-mapped graphics memory 72 of the invention is dynamic. This means that it must be accessed constantly and at very short intervals, i.e., about every two milliseconds or so. Otherwise, the image memory thereof will "fade" and lose its contents. As mentioned, there are two complete screens of memory: active and inactive. The action of the CRT controller chip 76 accessing memory to generate the image will constantly refresh the "active" screen memory. A means is provided also to access the "inactive" or "erased" screen memory so that it will stay erased. This means includes programming the CRT controller chip 76 to access 1024 pixels for each horizontal line, accessing thereby twice as many bits (one bit equals one pixel, and eight pixels equals one byte) of image data as are displayed on the screen 32 of the display monitor 10. An "every-other" circuit 126 (see FIG. 18) allows either only even numbered o only odd numbered bytes to be loaded into the pair of buffer RAMS 78. Extraneous data is ignored by the CRT controller chip 76 and dynamic RAM 114 access has been achieved. The even numbered bytes form one image screen memory, and the odd numbered bytes form the other.

The just described procedure keeps the dynamic memory of the dynamic RAM 114 regularly and constantly accessed when the same is under the control of the CRT controller chip 76. As the microprocessor 70 is randomly writing to the dynamic image memory of the dynamic RAM 114 (generating and/or erasing visual acuity targets), the microprocessor 70 is regularly interrupted by the interrupt circuitry 112 to allow control of the image memory to be briefly returned to the CRT controller chip 76, long enough for it to accomplish complete "memory refresh."

Figure 18:
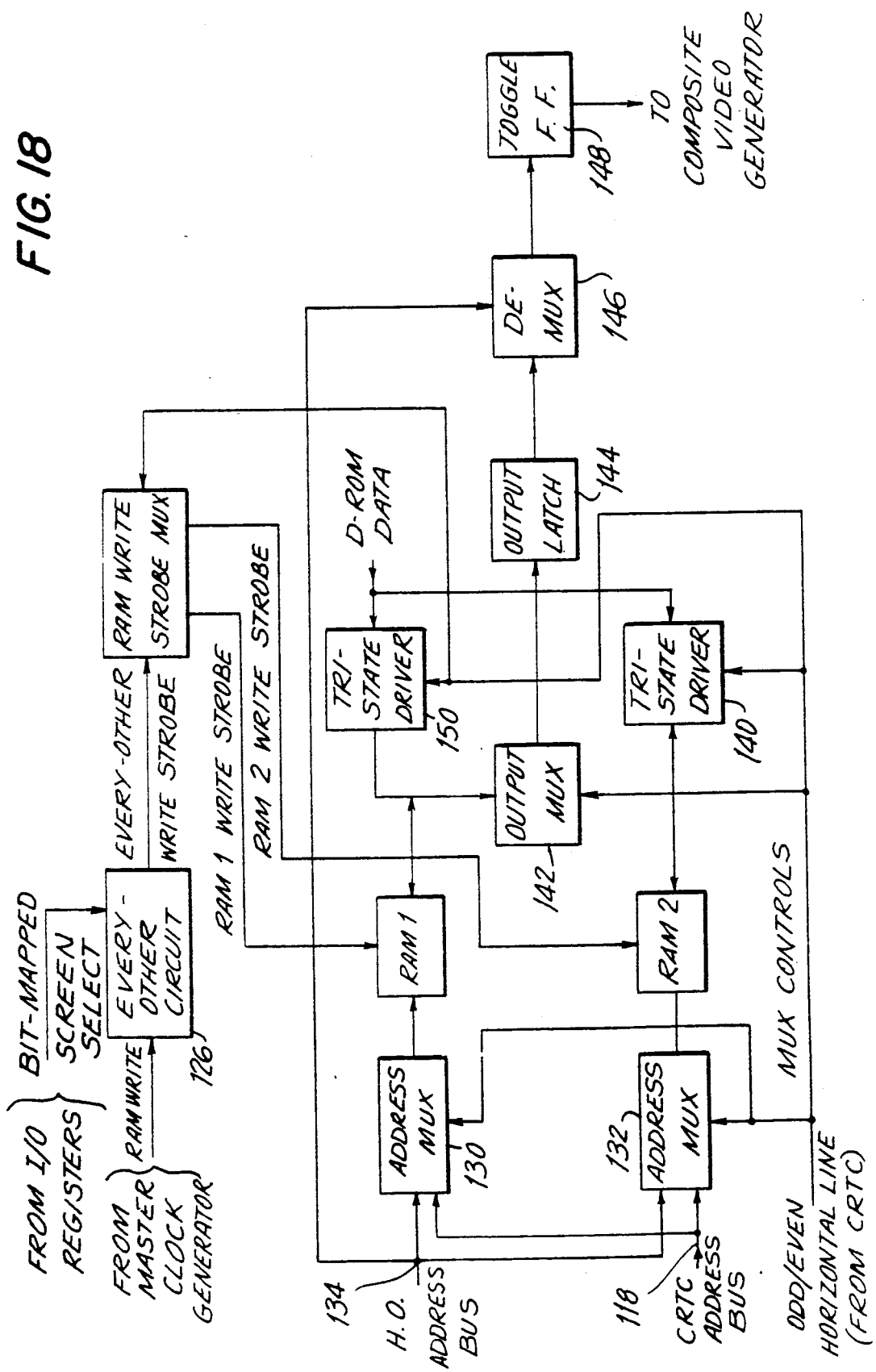
FIG. 18 is a block diagram of a third operative segment of the part illustrated in FIG. 14.

In FIG. 18 are depicted the operational blocks of the pair of buffer RAMS 78 comprising RAMS 1 and 2, each of which is being addressed via its address multiplexer 130 and 132 with signals arriving on a horizontal oscillator address bus 134 and on the CRT address bus 118. Multiplexer control signals from the CRT controller chip 76, signalling the odd/even instructions for the horizontal line, are admitted via lead 138 to the address multiplexers 130 and 132, to tri-state drivers 140 and 150 and its connection with an output multiplexer 142 coupling the respective outputs of the RAMS 1 and 2 to an output latch 144, and from there, via an eight-to-one demultiplexer 146 and a toggle flip-flop 148, to the composite video generator 82. Data from the dynamic RAM 114 are coupled to the RAMS 1 and 2 via tri-state drivers 140 and 150.

FIG. 19 illustrates in more detail the various connections to and from the CRT control chip 76, including inputs from a clock, the memory strobe and the "end-readout" strobe, and outputs including the CRT address bus 118, carrying signals to the interrupt circuit 112 and to the odd/even horizontal line 138, as well as to the horizontal and vertical synchronization and blank command of the I/O registers 110.

Details of the horizontal size oscillator 80 are illustrated in FIG. 20. Signals appearing on the microprocessor data bus 108 are latched into a start register 152, whose outputs are coupled to a first comparator 154, whose other inputs derive from the CRTC address bus 118, i.e., the LSBs mentioned above. The output of the comparator 154, a "start readout" signal, is coupled to a readout latch 156, which turns on and off a voltage controlled oscillator (V.C.O.) 158, which is coupled to a ten-bit counter 160. The V.C.O. 158 is provided with a horizontal size adjustment 162. The readout latch 156 also transmits reset signals directly to the counter 160 via lead 164. A second comparator 166, coupled to the horizontal oscillator address bus 134 via lead 170, detects the final horizontal pixel address providing the end readout signal to the readout latch 156 and to the CRTC 76 via lead 168.

Figure 21:
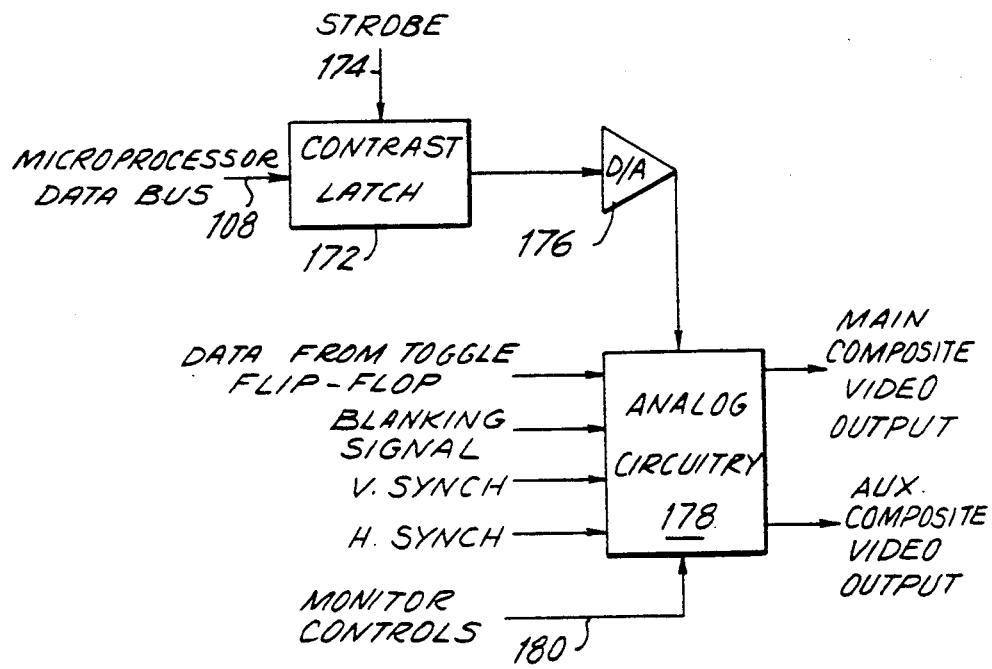
FIG. 21 is a block diagram of a sixth operative segment of the part illustrated in FIG. 14.

In FIG. 21, the construction of the composite video generator 82 is illustrated. It comprises a contrast register 172, receiving signals via the microprocessor data bus 108 and strobe signals via lead 174, and transmitting to a digital to analog converter 176, which relates the converted signals to an analog circuitry 178. Other inputs to the analog circuitry 178 are data arriving from the toggle flip-flop 148, blank signal and vertical and horizontal synchronization from the CRT control chip 76, and monitor controls via lead 180, see FIG. 16. The composite video output of the analog circuitry 178 is fed directly to the CRT display monitor 10, and to an auxiliary CRT display monitor, not shown, if there is one.

Figure 22:
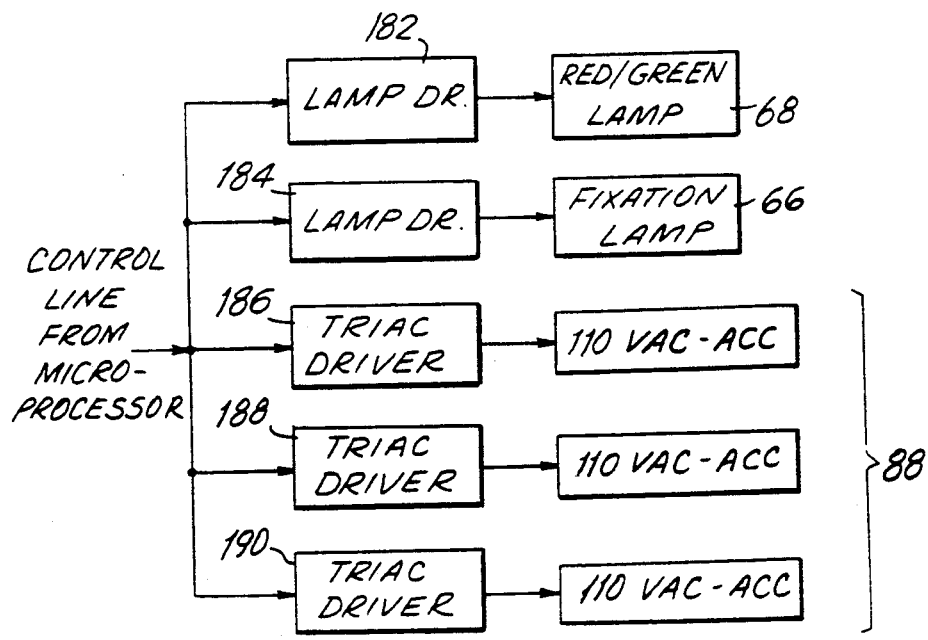
FIG. 22 is a block diagram of a seventh operative segment of the part illustrated in FIG. 14.

Details of the accessory controls 86 are illustrated in FIG. 22 and include two lamp drives 182 and 184 to drive the red-green display 68 and the fixation light 66, respectively; and three gate-controlled semiconductor switch drivers (TRIAC drivers, trademark of G.E. Company) 186, 188 and 190, to provide the three 110 V.A.C. outlets 88 for any accessories, observe FIG. 2.

Details of the power control 84 are illustrated in FIG. 23 and include the hand-controller on/off switch 60 monitor, an automatic off latch 192 receiving automatic-off bits from the microprocessor 70, a TRIAC driver 194 providing both a 110 V.A.C. outlet 196 to the display monitor 10 and a +5 V dc regulated power supply 198 to provide logic power to the circuitry within base unit 12. 110 V.A.C. power from a conventional household outlet is first admitted to an AC/DC converter 200, to generate an unregulated +12 V dc supply, and via a power switch 202 to certain other components, other than logic components, and to the hand-held remote control unit 14.

The construction of the hand-held remote control unit 14 is illustrated in FIG. 24 and essentially comprises the keyboard 18, the liquid crystal display unit 16, and an electro-luminescent driver 204 for the electro-luminescent panels 206. The keyboard 18 itself includes a cross matrix membrane switch 208, a keyboard encoder 210 and a line driver 212 to provide serial data to the microprocessor 70. The liquid crystal display 16 receives LCD data from the microprocessor 70 to an LCD driver 214, driving both the display unit 16 and a beeper 216.

Details of the LCD driver 214 are illustrated in FIG. 25 and include a line receiver 218, a bit clock and a burst clock generator 220 and 222, all three connecting to a serial to parallel converter 224. The serial to parallel converter 224 is coupled to a beeper driver 226 to drive the beeper 216, and to LCD driver IC's 228. A strobe generator unit 230 is driven by the burst clock generator 222, and strobes the parallel data from the converter 224 into LCD driver IC's 228. A plurality of LCD voltage driver generators 232, having an LCD contrast adjustment 234, are coupled to the LCD 16 via the IC's 228, to drive the liquid crystal display unit 16.

Details of the electro-luminescent driver 204 are illustrated in FIG. 26 and include a power control circuitry 236, with an electro-luminescent intensity adjustment 238, and a DC/AC converter 240 to drive both an LCD display panel 242 and a keyboard panel 244.

Figure 27A:
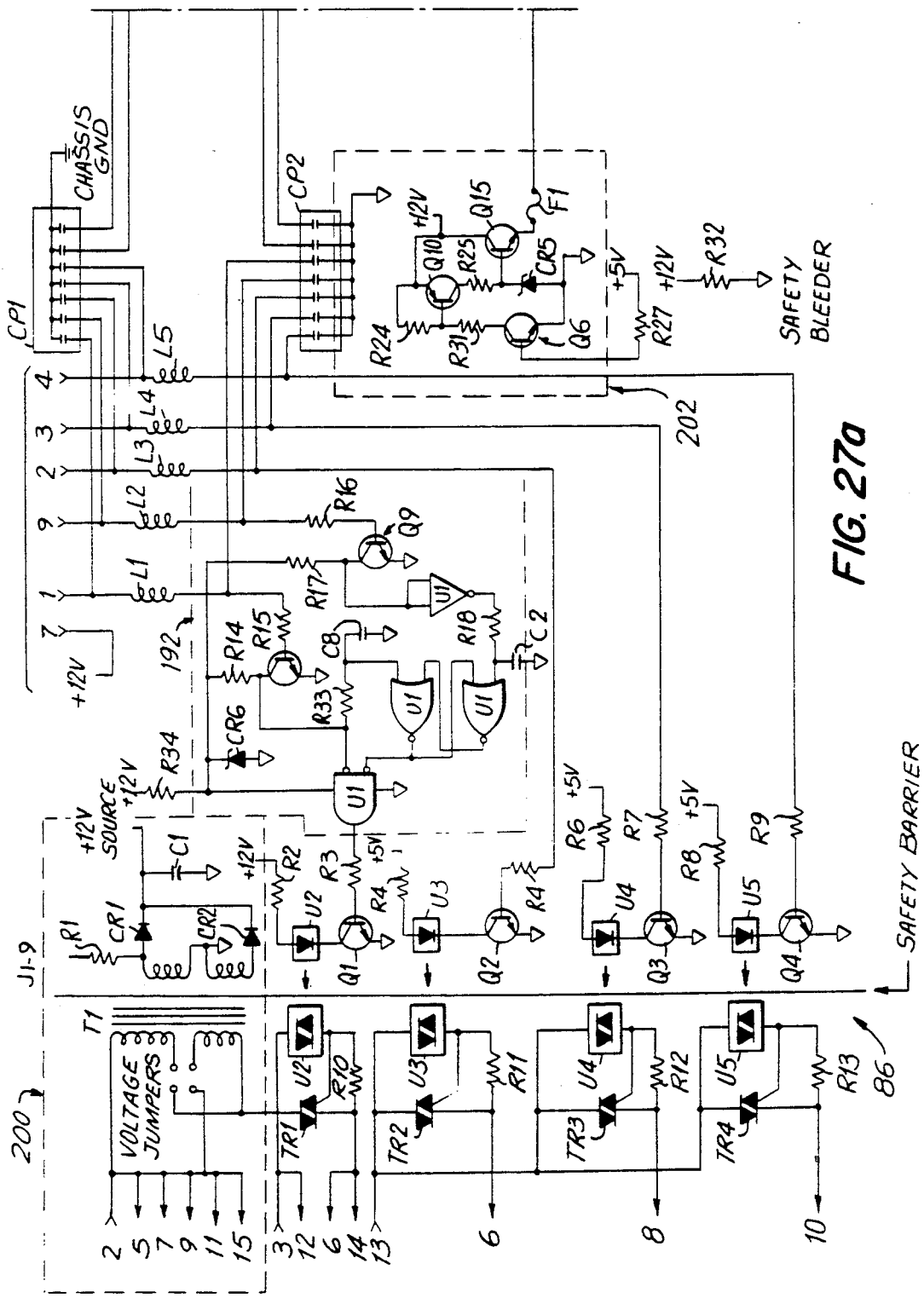
FIGS. 27a and 27b (hereinafter collectively referred to as FIG. 27) are schematic circuit diagrams of certain operative segments of one of the two operative parts illustrated in FIG. 1.
Figure 27B:
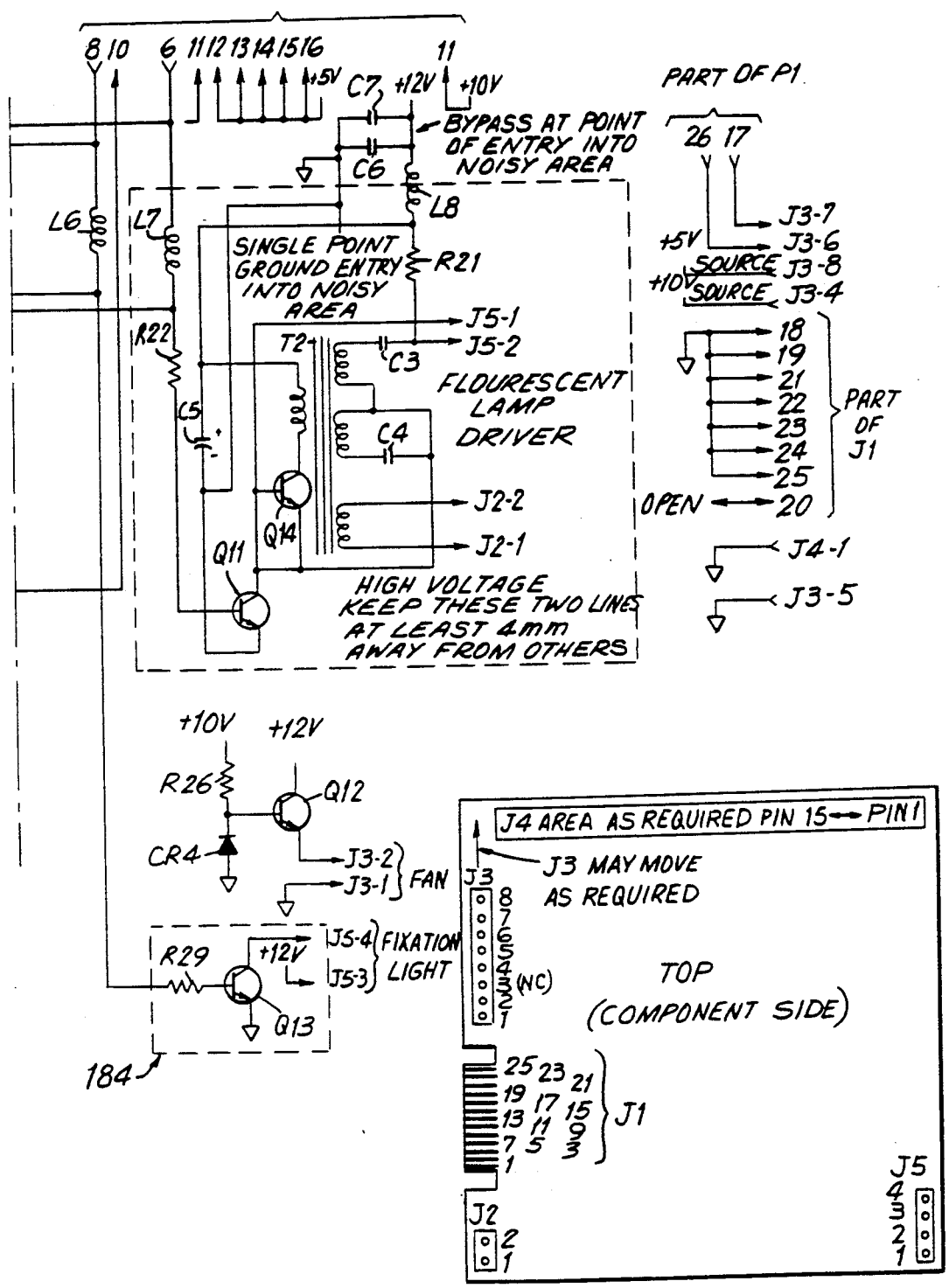
Figure 28A:
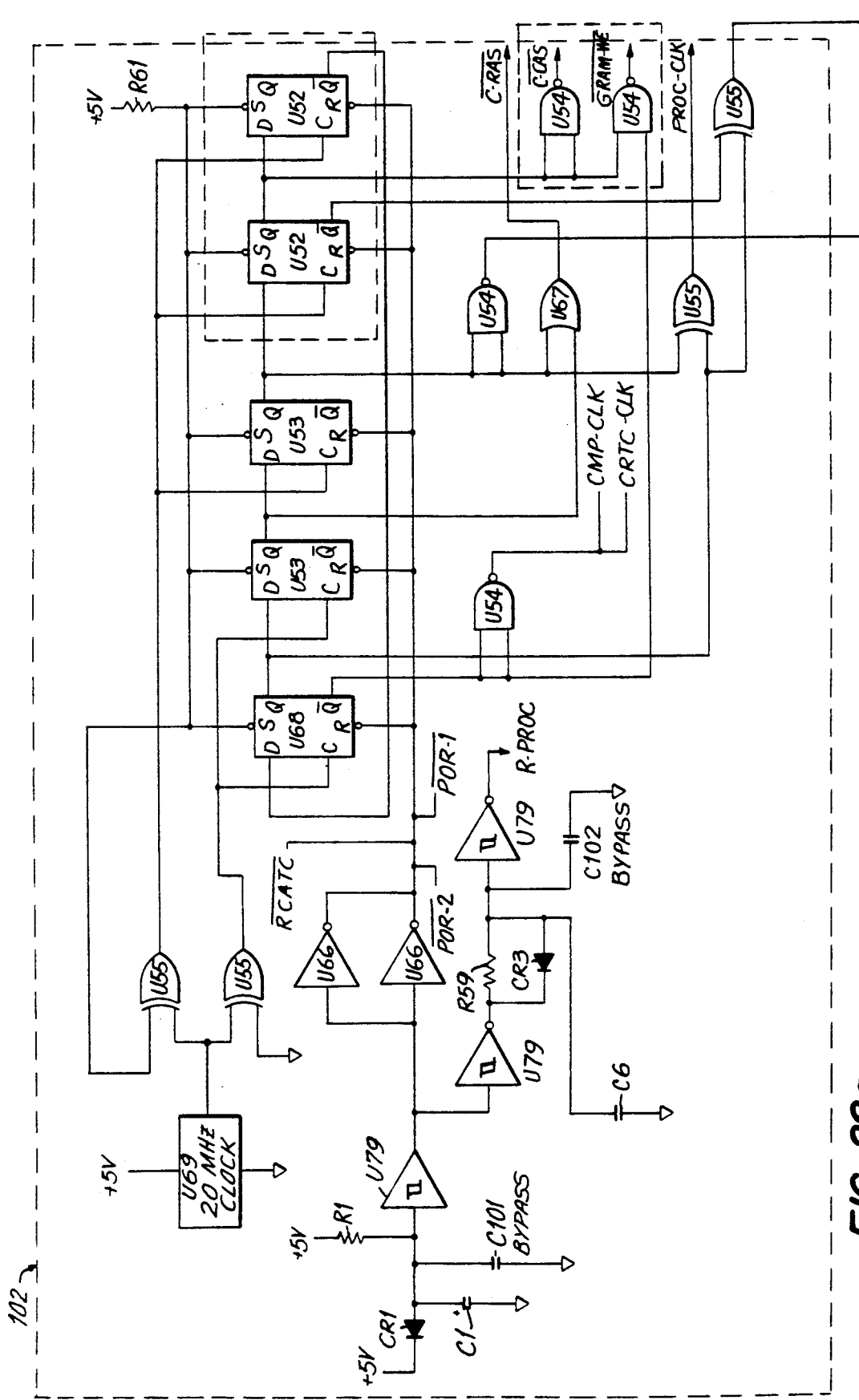
Figure 28B:
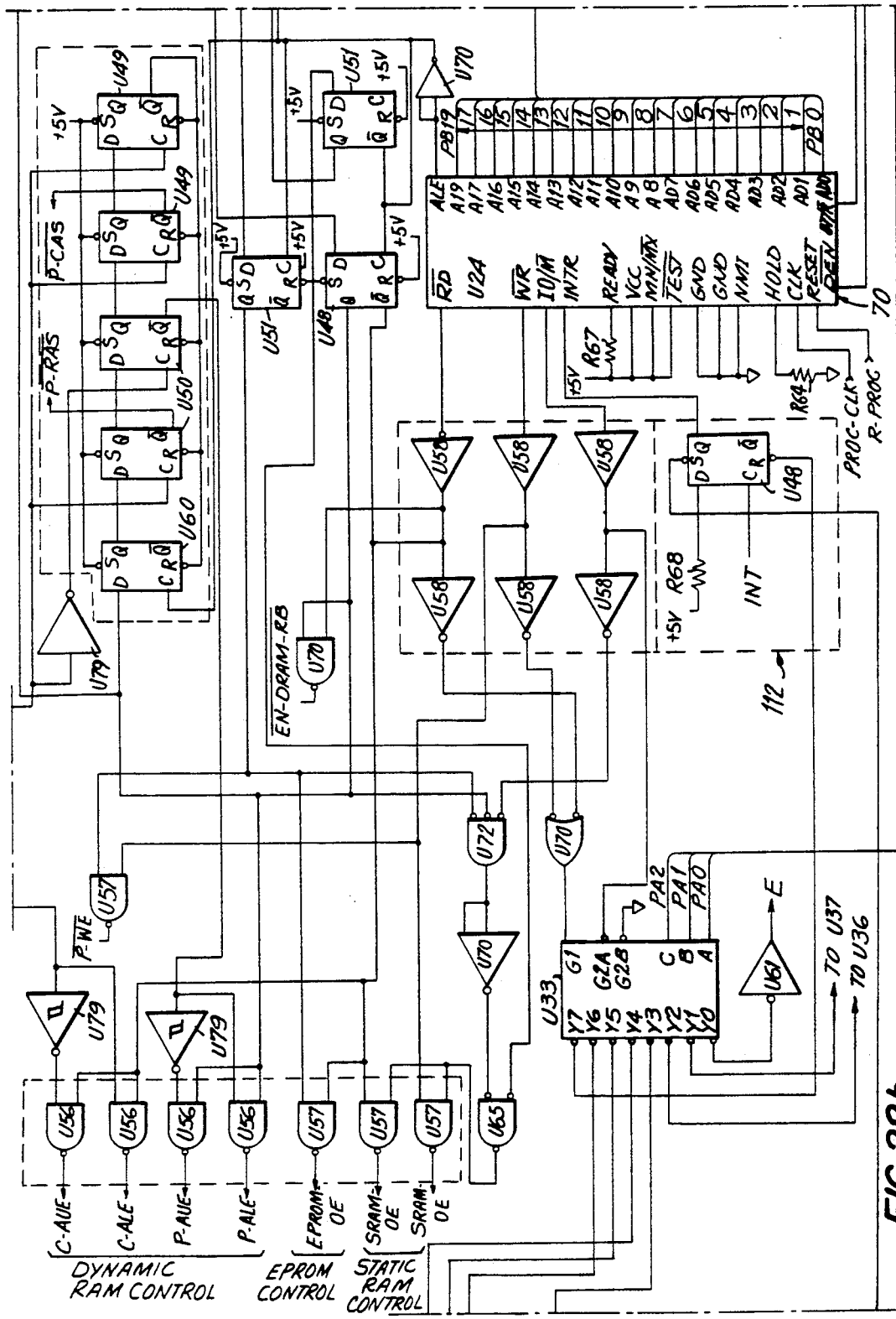
Figure 28C:
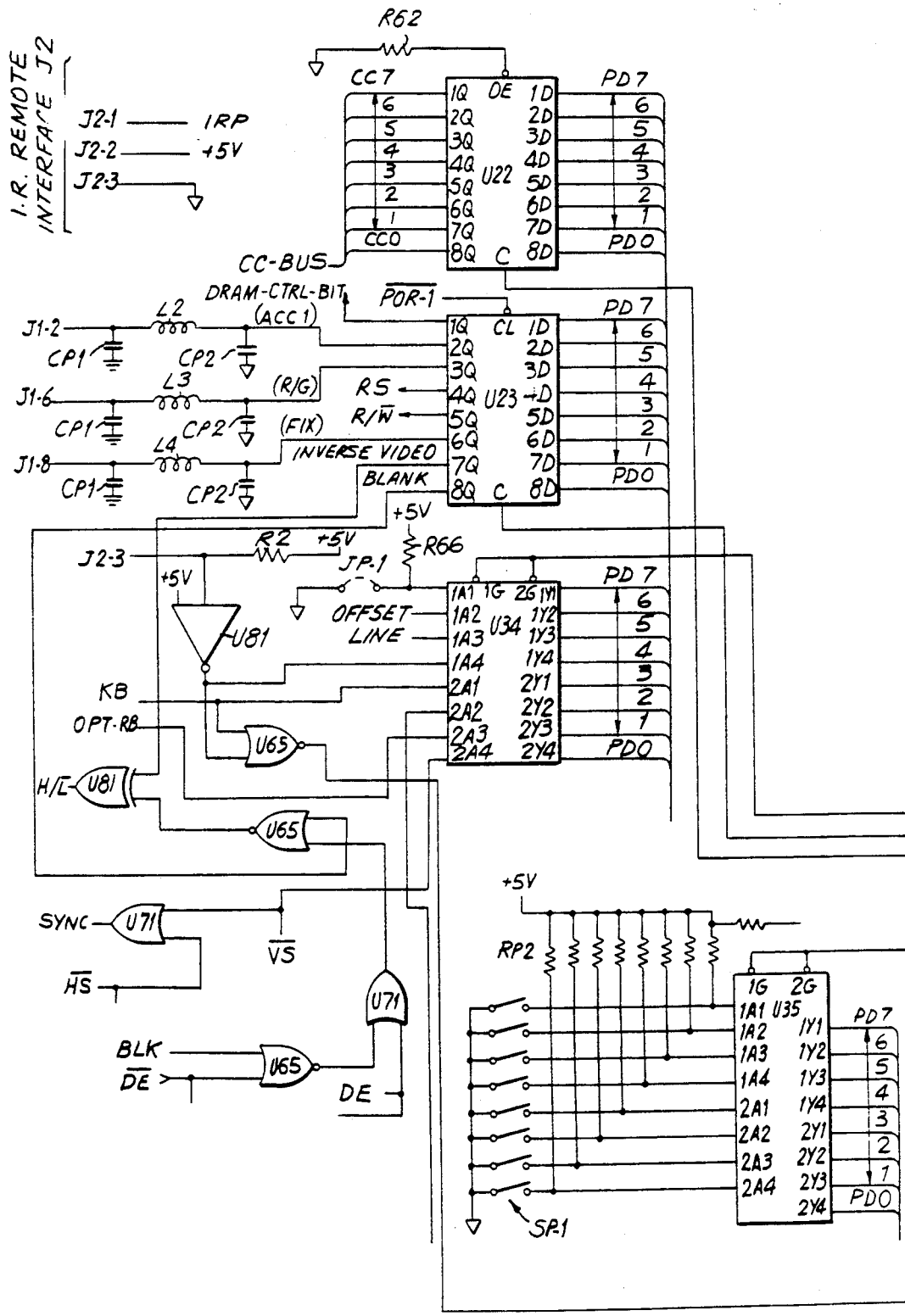
Figure 28D:
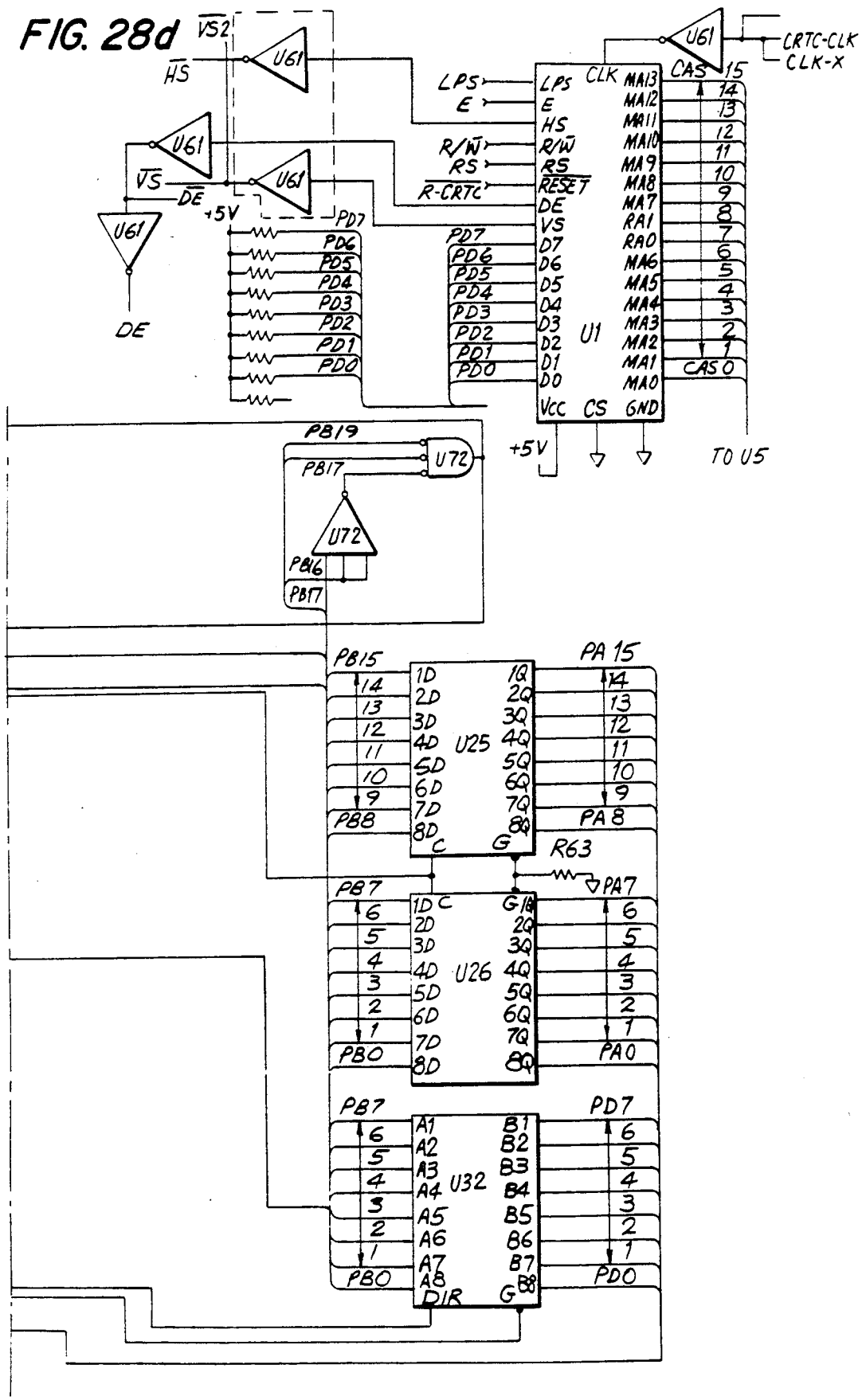
Figure 29B:
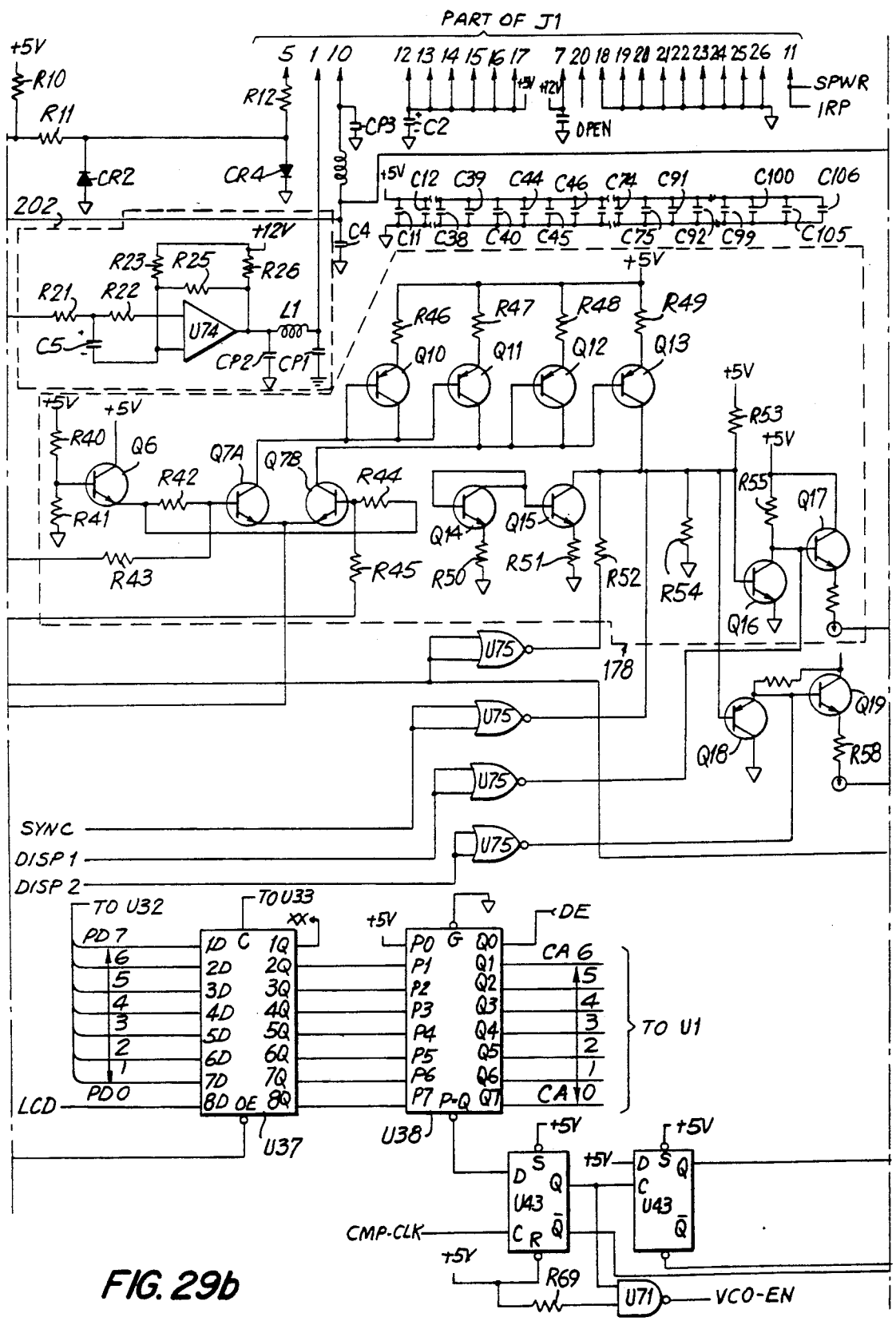
Figure 30A:
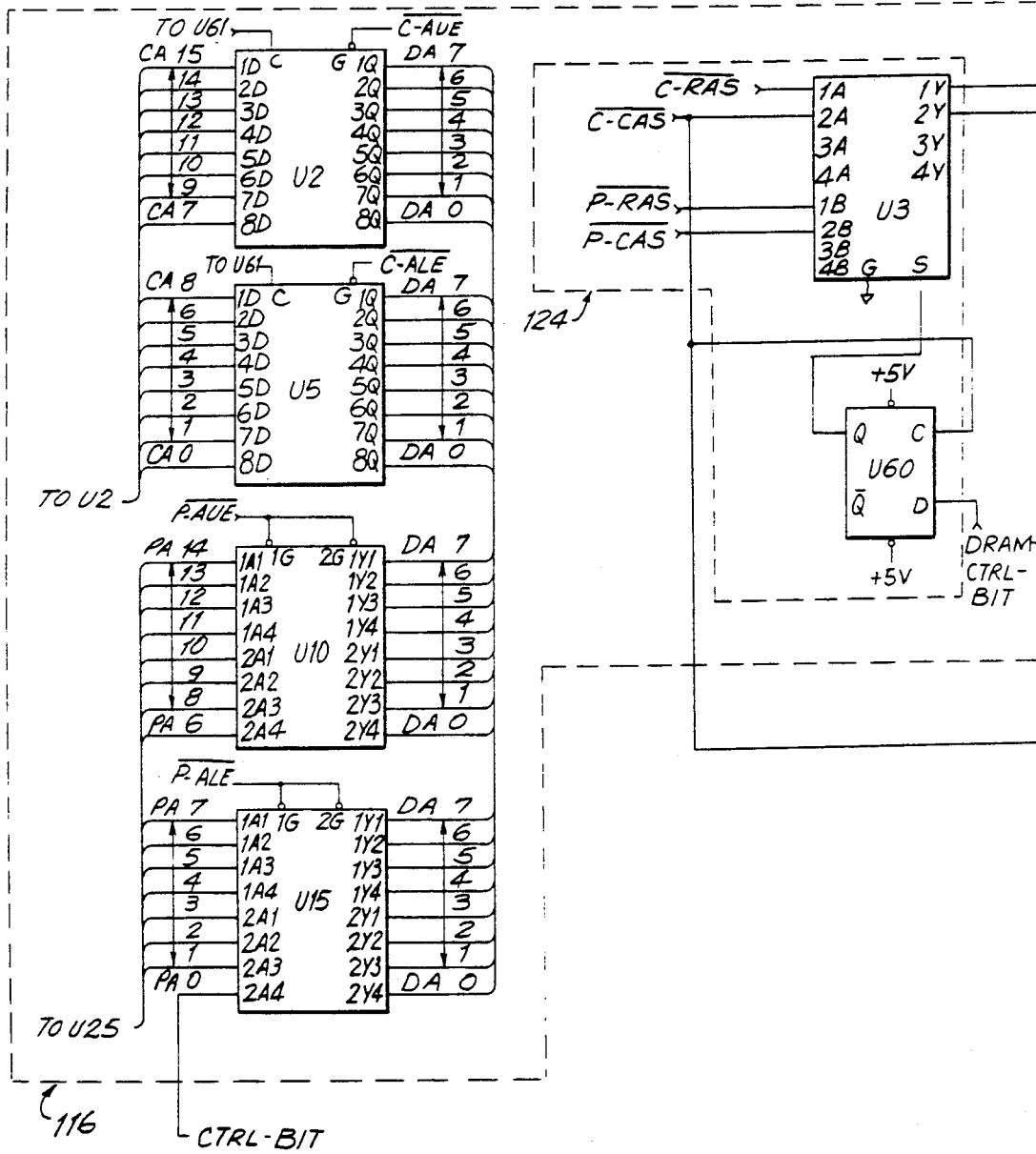
Figure 30B:
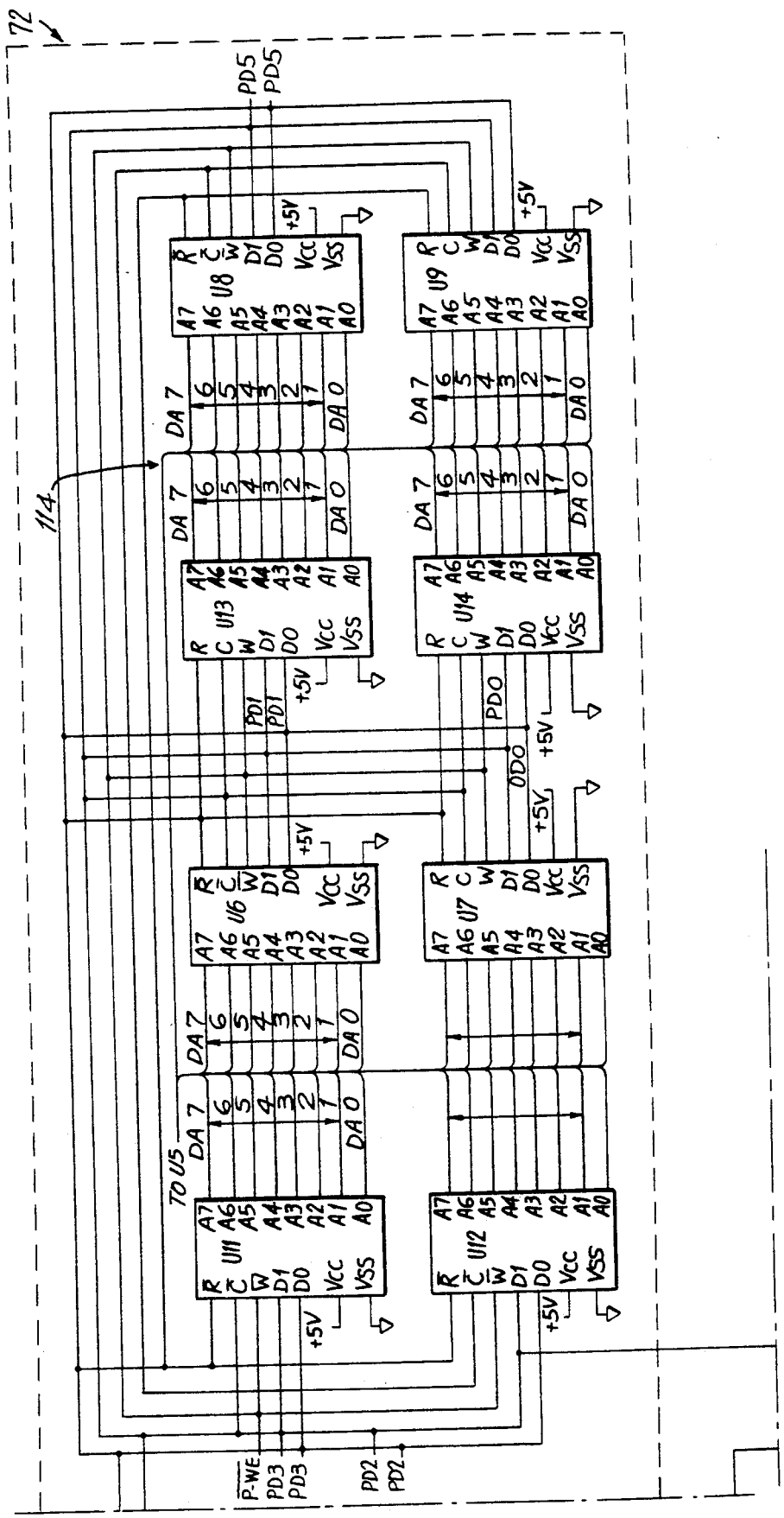
Figure 30C:
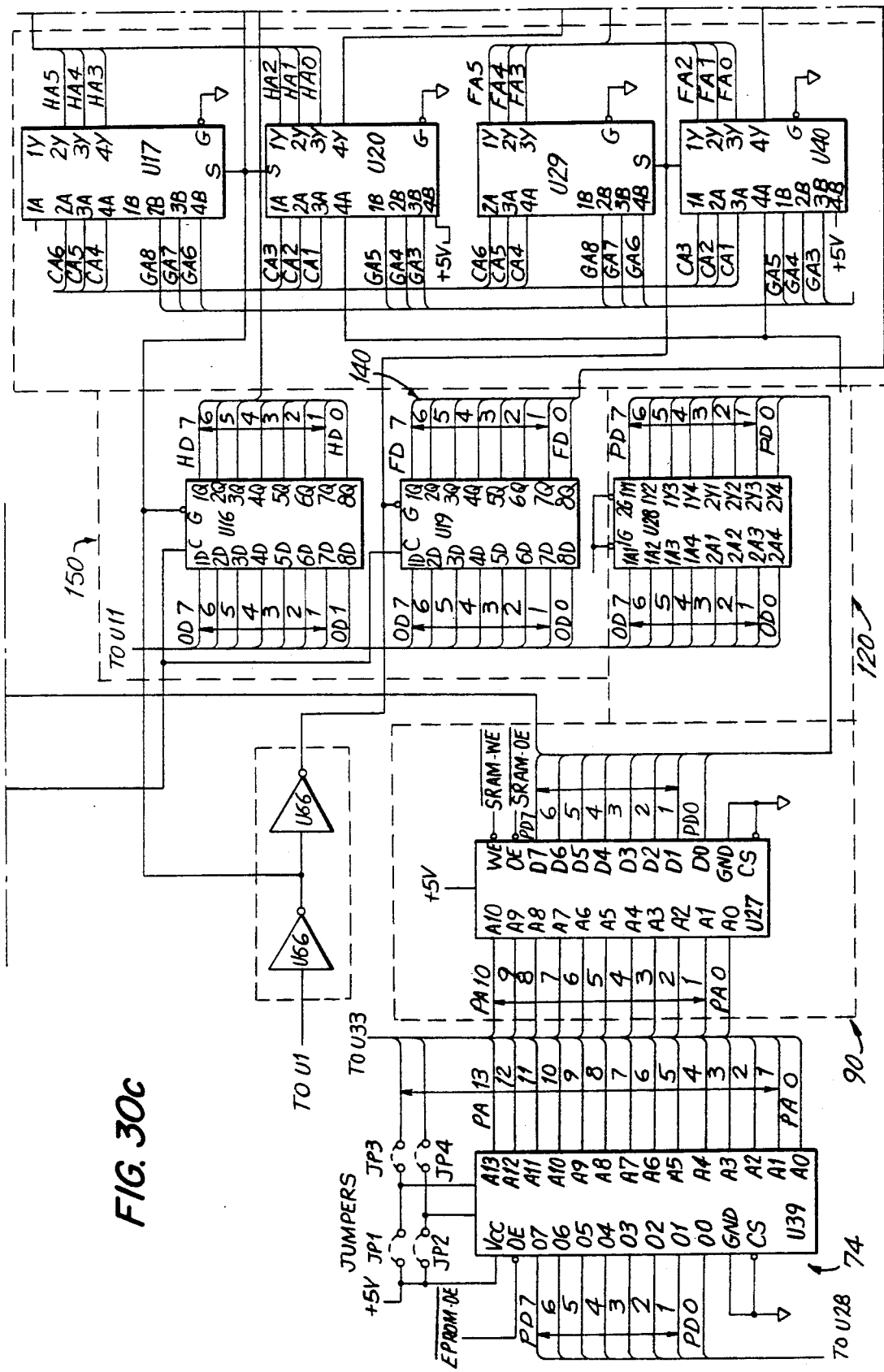
Figure 30D:
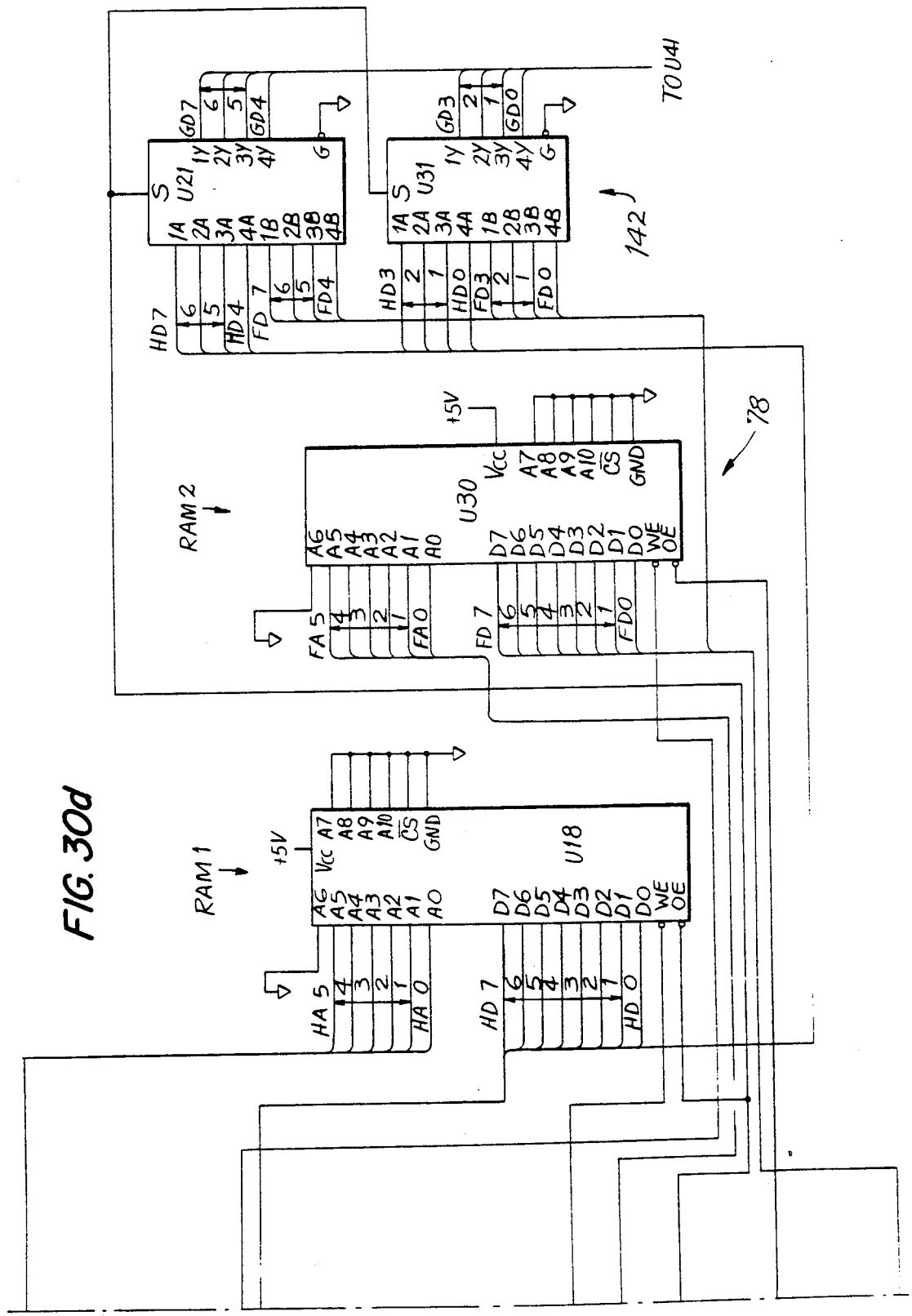
Figure 3I:
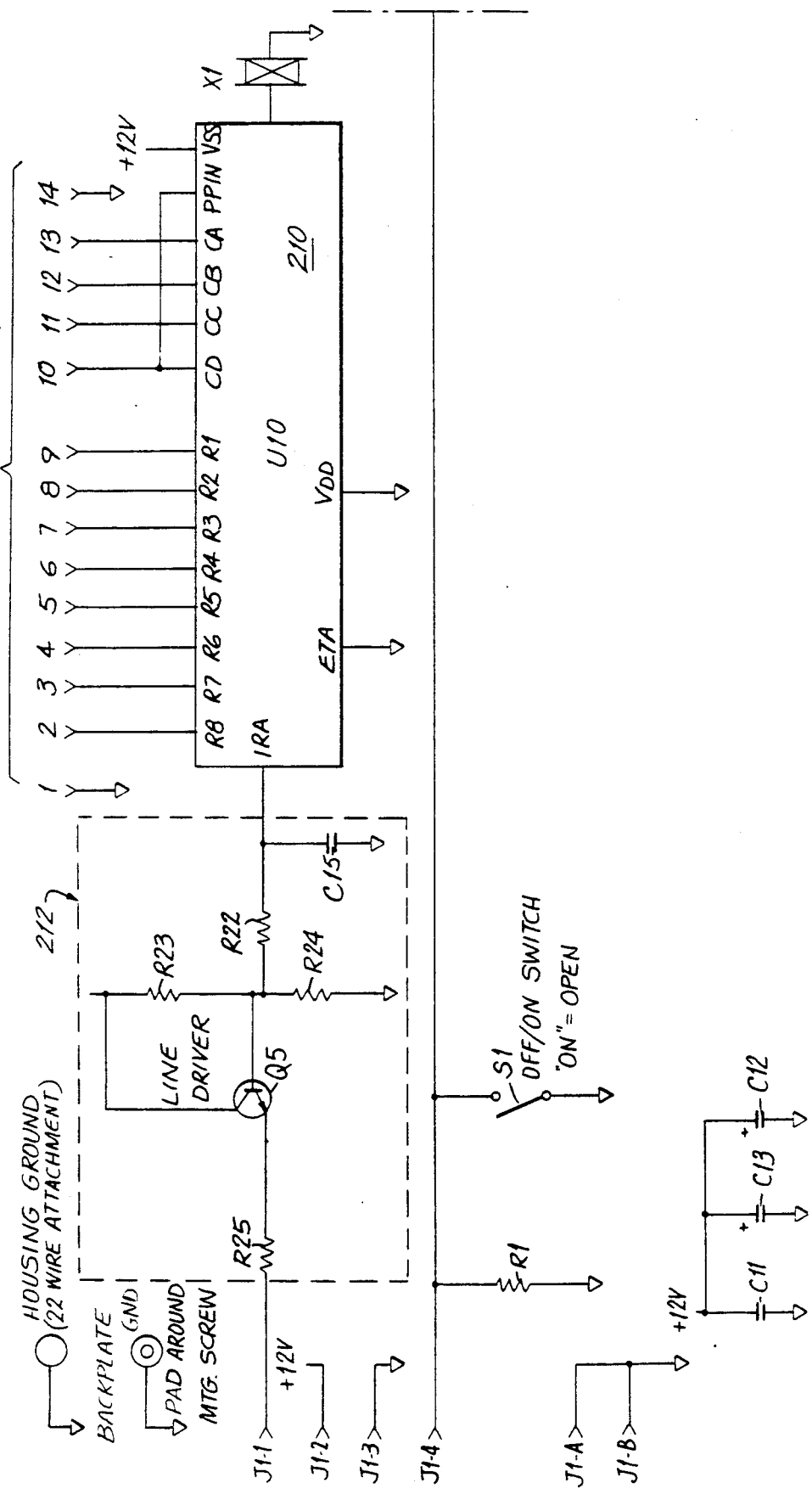
Figure 31B:
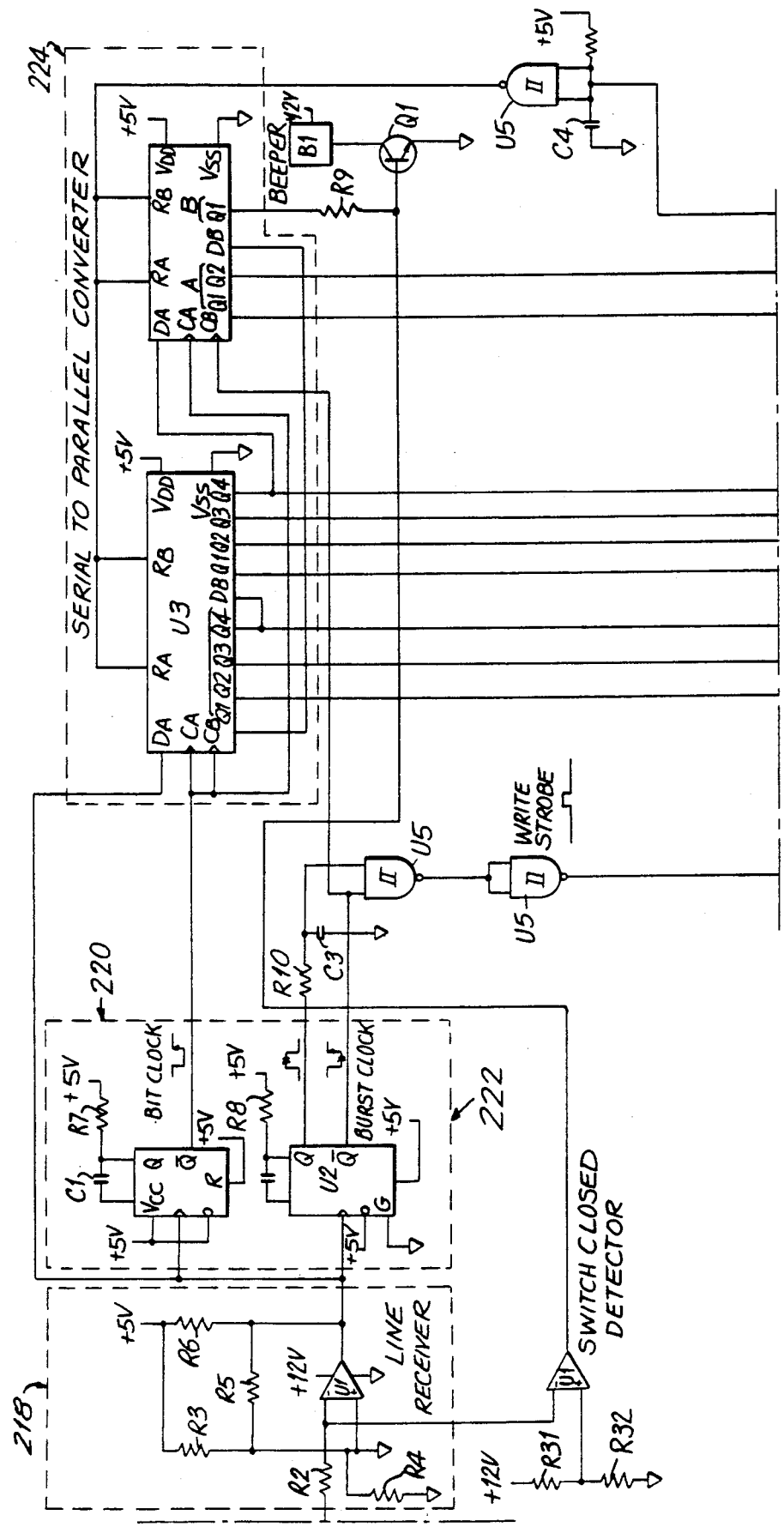
Figure 31D:
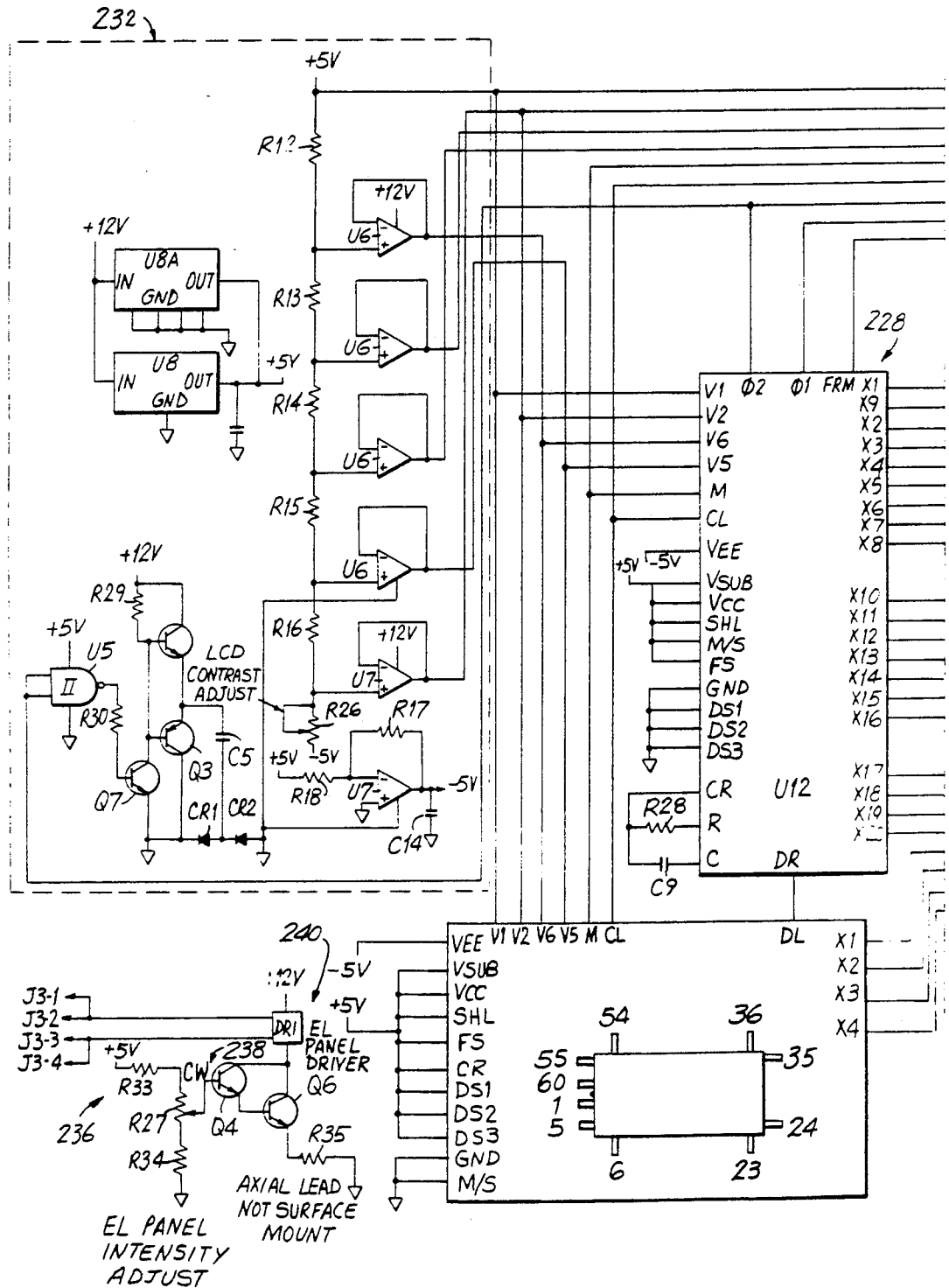

FIGS. 27 through 31 are detailed schematic circuit diagrams, in which certain of the above mentioned components have been identified by the same reference characters to further aid their understanding to those skilled in the art. In all other respects, various other components in these schematic circuit diagrams are standard off the shelf components, connected in one preferred configuration. They can also be interconnected in any number of ways to accomplish the tasks described within, as will be evident to those skilled in the art. Specifically, FIG. 27 illustrates the circuit diagram of a power p.c. board; FIGS. 28, 29 and 30 illustrate the circuit diagram of a microprocessor p.c. board; and FIG. 31 illustrates the circuit diagram of the hand-held remote control unit 14.

Another feature of the visual acuity tester of the invention resides in the contrast control of certain of the visual acuity targets appearing on the display monitor 10. With contrast being reduced, the horizontally scanning CRT beam is rendered to be only "part-way On." This reduced contrast is effected with the aid of the contrast latch 172, the D/A converter 176 and the analog circuitry 178 of the composite video generator 82, observe FIG. 21.

In operation, the microprocessor 70 is interrupted in its random generation of visual acuity targets anytime it receives a command from the hand-held remote control unit 14. A software program written into the ROM 74 constantly monitors activity on the lead connecting the hand-held remote control unit 14 to the microprocessor 70 and translates any serial data into an appropriate command signal to the microprocessor 70. Simultaneously therewith, another software program, also written into the ROM 74, generates a serial bitstream from the microprocessor 70 to the liquid crystal display 16 of the hand-held remote control unit 14, which serial bitstream corresponds to the microprocessor response to the command signal to the microprocessor 70. Consequently, the information displayed on the patient display monitor 10 will be the same as displayed for the examiner on the display unit 16 of the hand-held remote control unit 14.

As mentioned, the switch 64 of the hand-held remote control unit 14 is designed to turn off all power to the visual acuity tester, save power to a switch monitoring circuitry 60, observe FIG. 23. The microprocessor 70 also can turn the power off to the visual acuity tester, again excepting the switch monitoring circuitry, by sending an auto-off bit to the auto-off latch 192 of the power control 84, observe FIG. 23. Following such an automatic shutoff, the switch 64 on the hand-held remote control unit 14 must first be toggled "Off," then toggled "On" again to restore power to the entire system.

As mentioned, the hand-held remote control unit 14 is connected to the means 12 for generating the plurality of visual acuity targets via a long, flexible cable 34. Preferably, cable 34 is a forty-foot, four-conductor, telephone-style cable. The cable 34 transmits power to the hand-held control unit 14, transmits a serial bitstream to the microprocessor 70 whenever a control key is pressed on the keyboard 18, and transmits serial data from the microprocessor 70 to control the liquid crystal display unit 16 and the audio beeper 216.

Preferably, the keyboard 18 on the hand-held remote control unit 14 comprises the cross-matrix membrane switch 208 (FIG. 24) which, together with the keyboard encoder 210, generates the serial bitstream to be transmitted, with the aid of the line driver 212, down the cable 34 for interpretative and subsequent action by the microprocessor 70. Serial data is transmitted to the LCD driver circuitry 214 by the microprocessor 70. This data is in the form of "bursts" of ten pulse-width modulated bits generated by the microprocessor 70, observe FIG. 25. The serial bits are collected and converted to a ten-bit parallel signal by the serial to parallel converter 224 and presented as commands and data via the LCD driver I/Os 228 to the LCD 16 as well as to the beeper circuitry 216. The audio beeper 216 is used to provide audio feedback whenever a control key is pressed on the keyboard 18 of the hand-held remote control unit 14. The audio beeper 216 also is used to warn the operator of errors when the visual acuity tester of the invention is used as a calculator to perform optic-specific calculations, when the LCD display unit 16 of the hand-held remote control unit 14 becomes the display for the calculator, as illustrated in FIG. 10.

To enter the mode for calculating prescriptions, press "SHIFT" 18a, then "SUM Rx" 18d on the keyboard 18. The display unit 16 will display +0.00, +0.00 and 90 (or +0.00, −0.00 and 180) as starting values for sphere, cylinder and axis values respectively, note FIG. 10(a). Next, key in the value of any prescription component by pressing the appropriate digit keys, [.] (decimal point) and [±] sign as with any electronic calculator. The value will appear along the bottom of the hand controller display 16 as it is keyed, observe FIG. 10(b). After keying and verifying the value and sign of the component, press "SPH" key 18(e), "CYL" key 18(f) or "AXIS" key 18(c) as appropriate to enter the value and move it to its position in the display, observe FIG. 10(c). Perform this process for the sphere power, cylinder value and axis of the first prescription. When the first prescription has been entered and verified, press "SUM Rx" key 18(d). The word SUM will then appear on the display unit 16, along with the first prescription values. Enter the second prescription values in the same manner as the first prescription. When both prescriptions have been entered and verified and/or corrected by pressing "C" key 18(g), press "SUM Rx" key 18(d) again. The word SUM will again appear on the display, along with the sum of the two prescriptions. After a prescription has been calculated, press the "SHIFT" key 18(a) as many times as needed (usually two or three) to clear the prescription values from the hand controller display unit 16 and restore the primary functions to the keyboard 18.

The visual acuity tester of the invention also is adapted for measuring generalized visual sensitivity in terms of contrast sensitivity and spatial frequency response. A vision sensitivity apparatus by which the concurrent effects of contrast sensitivity and spatial frequency are ascertained is disclosed in U.S. Pat. No. 4,365,873, granted to Ginsburg on Dec. 28, 1982. In the Ginsburg apparatus, a visually perceptible chart, having a multiplicity of patches, is employed. In contrast, the visual acuity tester of the invention, when employed to measure generalized visual sensitivity, is designed to display, on the screen 32 of the display monitor 10, one pattern at a time of a plurality of patterns, in which each pattern comprises a grating of alternating light and dark regions and possessing differing contrast luminance and/or spatial frequency. The orientation of the gratings between successive grating patterns displayed is random to eliminate guesswork by patients.

Thus it has been shown and described an improved visual acuity tester, which improved visual acuity tester satisfies the objects and advantages set forth above.

Since certain changes may be made in the present disclosure without departing from the scope of the present invention, it is intended that all matter described in the foregoing specification or shown in the accompanying drawings, be interpreted in an illustrative and not in a limiting sense.

What is claimed is:

1. A visual acuity tester comprising:
   (a) a display monitor for displaying visual acuity targets, including means for generating a horizontally scanning beam; and
   (b) means for generating a plurality of visual acuity targets to be displayed on said monitor, said means for generating said plurality of visual acuity targets comprising:
   a bit-mapped graphics memory having means for storing a data bit corresponding to each pixel of lest one screen of a display; and
   means for turning on said horizontally scanning beam upon detecting the first bit being set in a horizontal row of said graphics memory and turning off said horizontally scanning beam upon detecting the second bit being set in said horizontal row.

2. The visual acuity tester of claim 1 wherein said display monitor is a raster scanned cathode ray tube, and said means for generating said plurality of visual acuity targets is a microprocessor based unit.

3. The visual acuity tester of claim 1 wherein said bit-mapped graphics memory is provided with two screens of memory: an active screen and an inactive screen, and a microprocessor coupled to said memory and designed to read from and write to said memory.

4. The visual acuity tester of claim 3 wherein said means for generating said plurality of visual acuity targets further includes a controller device designed to generate addressing, synchronization and blanking signals to produce a full screen size image on said display monitor.

5. The visual acuity tester of claim 4 further including means to vary said full screen size image on said display monitor so as to adapt said visual acuity tester for use with varied refracting distances from about ten to about twenty feet in length.

6. The visual acuity tester of claim 5 wherein said means for varying said full screen size image on said display monitor includes a pair of buffer RAMS designed to be read out to said display monitor at a variable rate of speed, producing thereby a variable sized image on said display monitor.

7. The visual acuity tester of claim 6 wherein said means for generating said plurality of visual acuity targets further includes a ROM containing a program memory and coupled to said microprocessor, a composite video generator coupled to said pair of buffer RAMS and controlled by said controller device, a RAM having two-way communication to said bit-mapped graphics memory via said microprocessor to achieve said two screens of memory, a power control coupling said microprocessor to a hand-held remote control unit, and a horizontal size oscillator coupled to said pair of buffer RAMS.

8. The visual acuity tester of claim 7 wherein said bit-mapped graphics memory includes an address multiplexer, a dynamic RAM coupled thereto, and a tri-state buffer coupling said pair of buffer RAMS to said dynamic RAM, and wherein said pair of buffer RAMS are coupled via an output latch, a demultiplexer and a toggle flip-flop to said composite video generator.

9. The visual acuity tester of claim 7 wherein said horizontal size oscillator includes at least one comparator, at least one latch coupled to said comparator, a voltage controlled oscillator provided with a horizontal size adjustment, and a ten-bit counter coupled to said latch.

10. The visual acuity tester of claim 7 wherein said composite video generator includes a contrast latch, a digital to analog converter and an analog circuitry coupled thereto to provide a composite video signal to said display monitor.

11. The visual acuity tester of claim 7 wherein said power control includes a manual on-off switch, an automatic off-latch coupled to said microprocessor and designed to receive auto-off bits therefrom and a gate-controlled semiconductor switch to provide A.C. power to said display monitor and D.C. power to said hand-held remote control unit.

12. The visual acuity tester of claim 7 wherein said horizontal size oscillator includes at least one comparator, at least one latch coupled to said comparator, a voltage controlled oscillator provided with a horizontal size adjustment, and a ten-bit counter coupled to said latch, wherein said composite video generator includes a contrast latch, a digital to analog converter, and an analog circuitry coupled thereto to provide a composite video signal to said display monitor, and wherein said power control includes a manual on-off switch, an automatic off-latch coupled to said microprocessor and designed to receive auto-off bits therefrom, and a gate-controlled semiconductor switch to provide A.C. power to said display monitor and D.C. power to said hand-held remote control unit.

13. The visual acuity tester of claim 3 further including means for effecting contrast control on said display monitor, said means including a register and an analog circuitry coupled to said register.

14. The visual acuity tester of claim 3 further including a red-green display, a fixation light and means for blanking the display monitor and lighting said fixation light following a first period of non-use of said tester.

15. The visual acuity tester of claim 11 further including means for automatically disconnecting all power to the visual acuity tester save to a switch monitoring circuitry in said means for generating said plurality of visual acuity targets following a second period of non-use of said tester.

16. The visual acuity tester of claim 3 further including means for effecting optical prescription calculations via said keyboard and displaying such calculations on said display unit of said hand-held remote control unit.

17. The visual acuity tester of claim 3 wherein said microprocessor is designed to receive clock pulses from a clock generator and interrupt signals from an interrupt circuitry, said interrupt circuitry being coupled to said keyboard of said hand-held remote control unit and designed to generate said keyboard interrupt signals to said microprocessor.

18. The visual acuity tester of claim 1 wherein said means for generating said plurality of visual acuity targets is provided with a plurality of switch settings to determine the original character, background and appearance of said targets on said display monitor and on said display unit.

19. The visual acuity tester of claim 1 further including a floor stand for said display monitor and said means for generating said plurality of visual acuity targets; and a stand for said hand-held remote control unit designed to secure said unit therein, said stand being adapted to be placed on a horizontal surface and also to be secured to a vertical surface.

20. The visual acuity tester of claim 1 further comprising a hand-held remote control unit coupled to said means for generating comprising a display unit and a keyboard.

21. The visual acuity tester of claim 20 wherein said microprocessor is designed to receive clock pulses from a clock generator and interrupt signals from an interrupt circuitry, said interrupt circuitry being coupled to said keyboard of said hand-held remote control unit and designed to generate keyboard interrupt signals to said microprocessor.

22. The visual acuity tester of claim 20 wherein said display unit is a backlighted liquid crystal display unit, and wherein said keyboard also is backlighted.

23. The visual acuity tester of claim 22, further comprising:
   a liquid crystal driver for said liquid crystal display unit, said driver comprising a line receiver coupled to said microprocessor based unit, a serial to parallel converter coupled to said line receiver, a bit clock generator and a burst clock generator coupled to said line receiver and said converter, and designed to generate clock pulses to said converter, voltage generators coupled to said liquid crystal display, and a strobe generator connected to said burst clock generator designed to generate clock pulses to LCD driver IC's.

24. The visual acuity tester of claim 23 wherein said hand-held remote control unit further includes an electroluminescent driver to drive an electroluminescent panel on said keyboard, said driver comprising a power control circuitry provided with an electroluminescent intensity adjustment, and a DC to AC converter coupled to said circuitry.

25. The visual acuity tester of claim 22 wherein said hand-held remote control unit further includes a liquid crystal driver for said liquid crystal display unit, said driver comprising a line receiver coupled to said microprocessor based unit, a serial to parallel converter coupled to said line receiver, a bit clock generator and a burst clock generator coupled between said line receiver and said converter and designed to generate clock pulses to said converter, voltage generators coupled to said liquid crystal display driver, and a strobe generator connected to said burst clock generator and said converter.

26. The visual acuity tester of claim 22, further comprising a brightness adjustment means for both said display unit and said keyboard to accommodate user preference and room lighting conditions.

27. The visual acuity tester of claim 22, further comprising a contrast adjustment means for said display unit between a viewing angle range from about 15° to about 90°.

28. The visual acuity tester of claim 20, further comprising means for effecting optical prescription calculations via said keyboard and for displaying such calculations on said display unit of said hand held remote control unit, said optical prescription calculations including values for sphere power, cylinder value and axis.

29. The visual acuity tester of claim 28, further comprising:
an audio beeper to indicate the actuation of keys on said keyboard and to warn of errors when the visual acuity tester is used as a prescription calculator.

30. The visual acuity tester of claim 29 further comprising:
means for automatically disconnecting all power to the visual acuity tester save to a switch monitoring circuitry in said means for generating said plurality of visual acuity targets following a second period of non-use of said tester.

31. The visual acuity tester of claim 1, further comprising means for effecting contrast control on said display monitor, said means including a register and an analog circuit coupled to said register.

32. The visual acuity tester of claim 3 further comprising means to erase the visual acuity targets stored on said inactive screen of memory in preparation for said inactive screen to become active prior to a key on said keyboard being pushed to generate visual acuity targets to be stored on said newly active screen of memory.

* * * * *

UNITED STATES PATENT AND TRADEMARK OFFICE
CERTIFICATE OF CORRECTION

PATENT NO. : 5,121,981
DATED : June 16, 1992
INVENTOR(S) : Morey H. Waltuck et al.

It is certified that error appears in the above-identified patent and that said Letters Patent is hereby corrected as shown below:

Column 14:
    In claim 1, line 10, after "of" add -- at --, and change "lest" to -- least --.

Column 18:
    In claim 30, line 3, add the following paragraph before "means":   -- a red-green display, a fixation light, and means for blanking the display monitor and lighting aid fixation light following a first period of non-use of said tester; and --.

Column 10, line 54, change "o" to --or--.

Signed and Sealed this

Seventh Day of June, 1994

Attest:

BRUCE LEHMAN

Attesting Officer        Commissioner of Patents and Trademarks